US012281093B2

(12) United States Patent
Mazurov

(10) Patent No.: US 12,281,093 B2
(45) Date of Patent: Apr. 22, 2025

(54) 3-(1,2,3,6-TETRAHYDROPYRIDIN-2-YL) PYRIDINE GLUTARATE OR A PHARMACEUTICALLY ACCEPTABLE SOLVATE THEREOF

(71) Applicant: PHILIP MORRIS PRODUCTS S.A., Neuchatel (CH)

(72) Inventor: Anatoly Mazurov, Greensboro Guilford, NC (US)

(73) Assignee: Philip Morris Products S.A., Neuchatel (CH)

( * ) Notice: Subject to any disclaimer, the term of this patent is extended or adjusted under 35 U.S.C. 154(b) by 884 days.

(21) Appl. No.: 17/289,794

(22) PCT Filed: Dec. 17, 2019

(86) PCT No.: PCT/EP2019/085598
§ 371 (c)(1),
(2) Date: Apr. 29, 2021

(87) PCT Pub. No.: WO2020/127225
PCT Pub. Date: Jun. 25, 2020

(65) Prior Publication Data
US 2021/0395218 A1  Dec. 23, 2021

(30) Foreign Application Priority Data
Dec. 17, 2018  (EP) .................... 18213200

(51) Int. Cl.
*C07D 401/04* (2006.01)

(52) U.S. Cl.
CPC ........ *C07D 401/04* (2013.01); *C07B 2200/13* (2013.01)

(58) Field of Classification Search
CPC ..... C07D 401/04; C07B 2200/13; A61P 5/16; A61P 25/28; A61P 25/30; A61P 29/00; A61K 31/444
See application file for complete search history.

(56) References Cited

U.S. PATENT DOCUMENTS

| | | |
|---|---|---|
| 5,582,837 A | 12/1996 | Shell |
| 5,942,244 A | 8/1999 | Friedman |
| 5,972,389 A | 10/1999 | Shell |
| 6,090,411 A | 7/2000 | Pillay |
| 6,210,710 B1 | 4/2001 | Skinner |
| 6,217,903 B1 | 4/2001 | Skinner |
| 6,723,340 B2 | 4/2004 | Gusler |
| 7,832,410 B2 | 11/2010 | Hon |
| 8,207,346 B2 | 6/2012 | Puthiaparampil |
| 8,557,999 B2 | 10/2013 | Puthiaparampil |
| 9,387,201 B2 | 7/2016 | Williams |
| 2016/0030407 A1* | 2/2016 | Mullan ............... A61K 31/444 514/334 |
| 2018/0184704 A1 | 7/2018 | Williams |

FOREIGN PATENT DOCUMENTS

| | | | |
|---|---|---|---|
| WO | WO 02/098389 | 12/2002 | |
| WO | WO 02/098496 | 12/2002 | |
| WO | WO 03/095012 | 11/2003 | |
| WO | WO 2011/119722 | 9/2011 | |
| WO | WO-2011119722 A2 * | 9/2011 | ........... A61K 31/444 |
| WO | WO 2012/005885 | 1/2012 | |
| WO | WO 2013/032558 | 3/2013 | |
| WO | WO 2015/009500 | 1/2015 | |

OTHER PUBLICATIONS

Stahl et al. ("Handbook of Pharmaceutical Salts Properties, Selection, and Use", Wiley-VCH, pp. 1-374). (Year: 2002).*
Pourchez et al. Assessment of new-generation high-power electronic nicotine delivery system as thermal aerosol generation device for inhaled bronchodilators (International Journal of Pharmaceutics 518, 264-269). (Year: 2017).*
Office Action issued in Russia for Application No. 2021119530 dated May 23, 2023 (38 pages). English translation included.
Bastin, Richard et al.: "Salt selection and Optimisation Procedures for Pharmaceutical New Chemical Entities", Organic Process Research & Development, 2000, vol. 4, p. 427-435.
Bernstein, J., "Polymorphism of Molecular Crystals" Moscow, Science, 2007, Ch. 7.3.2. Bioavailability, pp. 324-330.
Byrn, Stephen et al., Pharmaceutical Solids: A Strategic Approach to Regulatory Considerations, Review, Pharmaceutical Research, 1995, vol. 12, No. 7, p. 945-954.
Caira, M.R., Crystalline polymorphism of organic compounds, Topics in Current Chemistry, Springer Verlag Berlin Heidelberg, 1998, V.198, p. 163-208.
Chemical Encyclopedic Dictionary. Editor-in-Chief I. L. Knunyants, Moscow, Soviet Encyclopedia, 1983, pp. 130-131.
Clinical pharmacokinetics: theoretical, applied and analytical aspects: a guide/Edited by V.G. Kukes. (Chapter 11.2 Relationship between crystalline structure of substance, pharmacokinetics and drug efficacy, I.G. Smirnova, V.V. Chistyakov), 432 p., 2009.
Kuznetsova, G.A., Methodological instructions, Irkutsk State University of Physical Education and Sport, Department of General Physics, 2005.
Litvitsky P.F. "Pathophysiology", 2003, Moscow, GEOTAR-MED, vol. 1, pp. 142-144, 192-200.
Morisette, Sherry L. et al., "High-through put crystallization: polymorphs, salts, co-crystals and solvates of pharmaceutical solids", Advanced drug delivery reviews, 2004, v.56, pp. 275-300.
Naga K. Duggirala et al., "Pharmaceutical cocrystals: along the path to improved medicines," Chem. Commun., 2016, vol. 52, p. 640-655.

(Continued)

*Primary Examiner* — Matthew P Coughlin
*Assistant Examiner* — Meghan C Heasley
(74) *Attorney, Agent, or Firm* — Mueting Raasch Group

(57) ABSTRACT

The present invention relates to 3-(1,2,3,6-tetrahydropyridin-2-yl)pyridine glutarate or a pharmaceutically acceptable solvate thereof, to a crystal thereof and to a polymorph of this crystal. It further relates to the medicinal use of each of these, in particular in the treatment or prophylaxis of substance addiction or inflammation.

16 Claims, 7 Drawing Sheets

(56) References Cited

OTHER PUBLICATIONS

Rodriguez-Spong Barbara et al., "General principles of pharmaceutical solid polymorphism: a supramolecular perspective", Advanced Drug Delivery Reviews, 2004, 56, p. 241-274 (pp. 262-263)/ DOI:10.1016/j.addr.2003.10.005.
Variankaval, Narayan, et al.: "From form to function: Crystallization of active pharmaceutical ingredients", AIChE, 2008, vol. 54(7), p. 1682-1688.
Atzrodt J. et al., *Bioorg Med Chem*, 20(18), 5658-5667, 2012.
Ayers, J. T.; Xu, R.; Dwoskin, L. P.; Crooks, P. A. A general procedure for the enantioselective synthesis of the minor Tobacco alkaloids nornicotine, anabasine, and anatabine, *The AAPS Journal* 2005; 7(3), Article 75.
Cheng, et al., *Biochem. Pharmacol.*, vol. 22, pp. 3099-3108 (19).
Crafl et al., *Exp Opin Therap Targets* 9:887-900, 2005.
Deo, N. M.; Crooks, P. A. Regioselective alkylation of N-(diphenylmethylidine)-3-(aminomethyl)pyridine: a simple route to minor tobacco alkaloids and related compounds. *Tetr. Lett.* 1996, 37 (8), 1137-1140.
Felpin, F.-X.; Vo-Thanh, G.; Robins, R. J.; Villieras, J.; Lebreton, J. Total synthesis of (S)-anabasine and (S)-anatabine. *Synlett* 2000, (11), 1646-1648.
Genisson, Y.; Mehmandoust, M.; Marazano, C.; Das, B. C. Chiral 1,2-dihydropyridines and 2,5-dihydropyridinium salt equivalents. Synthesis of (+)-anatabine and a chiral benzomorphane. *Heterocycles* 1994, 39(2), 811-818.
Hansch, et al., *J. Med. Chem.*, vol. 11, p. 1 (1968).
Hu et al., *Bioorgan Med Chem Lett* 17:414-18, 2007.
Minghetti, *Curr Opin Neurol* 2005; 18:315-21.
Modvig A et al., *J Org Chem*, 79, 5861-5868, 2014.
Mrak & Griffin, *Neurobiol Aging* 26:349-54, 2005.
Paris et al. (2013) *European Journal of Pharmacology* 698, 145-153.
Quan, P. M.; Karns, T. K. B.; Quin, L. D. Total synthesis of dl-anatabine. *Chemistry & Industry* (London, United Kingdom) 1964, (36), 1553.
Ralay et al,, *J Neurosci* 26:662-70, 2006.
Rossi, F. V.; Ballini, R.; Barboni, L.; Allegrini, P.; Palmieri, A. A practical and efficient synthesis of (±)-anatabine. *Synthesis* 2018, 50(9), 1921-1925.
Rouchaud, A.; Kem, W. R. A convenient racemic synthesis of two isomeric tetrahydropyridyl alkaloids: isoanatabine and anatabine. *Journal of Heterocyclic Chemistry* 2010, 47(3), 569-581.
Saloranta, T.; Leino, R. From building block to natural products: a short synthesis and complete NMR spectroscopic characterization of (±)-anatabine and (±)-anabasine. *Tetrahedron Letters* 2011, 52(36), 4619-4621.
Sheng el al., *Neurobiol Aging* 17:761-66. 1996.
Vezzani & Granata, *Epilepsia* 46: 1724-43, 2005.
Vezzani et al., *Epilepsia* 43:S30-S35, 2002.
William JS et al., *Journal of Labelled Compounds and Radiopharmaceuticals,* 53(11-12), 635-644, 2010.
Yang, C.-M.; Tanner, D. D. A simple synthesis of (±)-1,2,3,6-tetrahydro-2,3'-bipyridine (anatabine) and (±)-3-(2-piperidinyl)pyridine (anabasine) from lithium aluminum hydride and pyridine. *Canadian Journal of Chemistry* 1997, 75(6), 616-620.
PCT Search Report and Written Opinion for PCT/EP2019/085598 dated Jan. 23, 2020 (8 pages).
Extended European Search Report for Application No. 18213200.1 dated Mar. 29, 2019 (7 pages).
Giron, D., Thermodinamica Acta (1995) 1-594.
J. Garrido, Forma y estructura de los Cristales, capítulo V, página 204.
Raúl Moscoso. Propiedad Intelectual e Innovación Tecnológica en el Ecuador. Ed. Abya-Yala. 2000.
Profesor Otero José Manuel en su obra: "La invención y las excepciones a la patentabilidad en la Decisión 486 del Acuerdo de Cartagena". Conferencia sobre Patentes. Quito, 2000.
Fernando Fuentes Pinzón, "La moral, la ética y la bioética como limitantes sociales a la protección de las invenciones por la vía de las patentes" Frónesis. dic. 2006, vol. 13, No. 3.
Carlos Correa, Guidelines for the examination of pharmaceutical patents: developing a public health perspective, Jan. 2007.
García -Pelayo y Gross R., Larousse Diccionario básico de la lengua española. Ed. Larousse. Buenos Aires. Argentina .1979. Pág. 250.
Nies S. A., Spielberg S. P., Capitulo 3, Principios de Terapeutica. Gaceta oficial del Acuerdo de Cartagen, Lima, Oct. 12, 2001, Ano XVIII—Numero 722.
Office Action issued in Russia for Application No. 2021119530 dated Oct. 19, 2023 (27 pages). English translation included.
Office Action issued in Japan for Application No. 2021-534811 dated Oct. 26, 2023 (11 pages). English translation included.
M.D. Mashkovsky "Medicines", 14th edition, vol. 1, Moscow, 2001, P11.
Kharkevich D.A. Pharmacology:/Textbook, 2010, 10th edition, pp. 72-82.
Noriyuki Takata, Drug Substance Form Screening and Selection in the Drug Development Stage, Pharm Stage, 2007, vol. 6, No. 10, pp. 20-25.
Edited by C.G. Wermuth, supervised/translated by Hiroshi Nagase, The Practice of Medicinal Chemistry, 2nd Part, Technomics, Inc., 1999.
Edited by Noriaki Hirayama, Handbook of Organic Compound Crystal Preparation, Principles and Know-How, Maruzen Publishing Co., Ltd., 2008.
Written by Akira Ogata, Operating Methods for Chemical Experiments, 1st part, Nankodo Co., Ltd., 1963.
Carbon Compounds—Advances in Research and Application: Jun. 2013 Edition, 8 pages.
Office Action issued in Colombia for Application No. NC2021/0009186 dated Apr. 29, 2024 (7 pages).
Office Action issued in Korea for Application No. 10-2021-7015007 dated Oct. 27, 2024 (17 pages). English translation included.
Brittain, Harry G., "X-ray Diffraction III: Pharmaceutical Applications of X-ray Powder Diffraction", 14 Spectroscopy 16(7); Jul. 2001 (5 pages).

* cited by examiner

| Angle (2-Theta°) | Intensity (count) | Intensity (%) |
|---|---|---|
| 7.96 | 1605 | 41.4 |
| 10.907 | 637 | 16.4 |
| 13.291 | 1304 | 33.7 |
| 14.413 | 532 | 13.7 |
| 15.239 | 544 | 14 |
| 16.479 | 1956 | 50.5 |
| 17.933 | 1296 | 33.5 |
| 20.61 | 1535 | 39.6 |
| 20.977 | 1542 | 39.8 |
| 21.318 | 2579 | 66.6 |
| 21.927 | 3078 | 79.5 |
| 22.263 | 1520 | 39.3 |

| Angle (2-Theta°) | Intensity (count) | Intensity (%) |
|---|---|---|
| 22.792 | 686 | 17.7 |
| 23.246 | 1188 | 30.7 |
| 24.426 | 3873 | 100 |
| 24.769 | 832 | 21.5 |
| 25.804 | 878 | 22.7 |
| 26.707 | 953 | 24.6 |
| 27.534 | 526 | 13.6 |
| 28.076 | 623 | 16.1 |
| 29.861 | 658 | 17 |
| 30.989 | 555 | 14.3 |
| 33.171 | 657 | 17 |
| 34.836 | 1009 | 26.1 |

3-(1,2,3,6-TETRAHYDROPYRIDIN-2-YL) PYRIDINE GLUTARATE OR A PHARMACEUTICALLY ACCEPTABLE SOLVATE THEREOF

This application is a U.S. National Stage Application of International Application No. PCT/EP2019/085598 filed Dec. 17, 2019, which was published in English on Jun. 25, 2020 as International Publication No. WO 2020/127225 A1. International Application No. PCT/EP2019/085598 claims priority to European Application No. 18213200.1 filed Dec. 17, 2018.

The present invention relates to 3-(1,2,3,6-tetrahydropyridin-2-yl)pyridine glutarate or a pharmaceutically acceptable solvate thereof, to a crystal thereof and to a polymorph of this crystal. It further relates to the medicinal use of each of these, in particular in the treatment or prophylaxis of substance addiction or inflammation.

BACKGROUND

Inflammation is a protective response to harmful stimuli, such as oxidative stress, irritants, pathogens, and damaged cells. The inflammatory response involves the production and release of inflammatory modulators that heal injured tissue and destroy damaged cells, by directly or indirectly producing and/or signalling the release of agents that produce reactive oxygen species. Thus, an appropriate inflammatory response involves a balance between the destruction of damaged cells and the healing of injured tissue.

An unchecked inflammatory response can lead to oxidative stress and the onset of various inflammatory disease pathologies. In fact, inflammatory processes underlie a wide variety of pathologies, including immune and autoimmune diseases, gastrointestinal diseases, various types of cancer, vascular disorders, heart disease, and neurodegenerative diseases. There is a need in the art for agents that can reduce inappropriate levels of inflammation.

SUMMARY OF THE INVENTION

The present invention relates to 3-(1,2,3,6-tetrahydropyridin-2-yl)pyridine glutarate (herein also referred to as anatabine glutarate) or a pharmaceutically acceptable solvate thereof, to a crystal thereof and to a polymorph of this crystal. It further relates to the medicinal use of each of these, in particular in the treatment or prophylaxis of substance addiction or inflammation.

A pharmaceutical composition comprising a therapeutically effective dose of anatabine glutarate, a pharmaceutically acceptable solvate thereof, a crystal thereof and/or a polymorph of the crystal, can be administered to an individual to reduce a symptom or a disorder comprising an NFKB-mediated inflammatory component and/or to reduce the risk of developing such a disorder. The NFKB-mediated inflammatory component is preferably chronic inflammation which occurs, for example, in thyroiditis, cancer, arthritis, Alzheimer's disease, and multiple sclerosis. The therapeutically effective doses of anatabine glutarate, the pharmaceutically acceptable solvate thereof, the crystal thereof and/or the polymorph of the crystal may also be provided in an extended release formulation. In other embodiments, isolated forms of anatabine glutarate, a pharmaceutically effective solvate thereof, a crystal thereof and/or a polymorph thereof can be provided in a bottled water product comprising, for example, about 1 ml to about 2,000 ml purified water and from about 0.00001 to about 0.0001 wt % of anatabine glutarate. The claimed compound, crystal, polymorph and/or pharmaceutical composition can have a monoamine oxidase (MAO) inhibitory effect.

Additionally or alternatively, the compound, crystal, polymorph and/or pharmaceutical composition of the invention may have a STAT3 phosphorylation inhibition effect.

In particular, the present invention relates to the following embodiments:

1. A compound which is 3-(1,2,3,6-tetrahydropyridin-2-yl)pyridine glutarate or a pharmaceutically acceptable solvate thereof.
2. The compound according to embodiment 1, wherein the 3-(1,2,3,6-tetrahydropyridin-2-yl)pyridine glutarate has a 1:1 molar ratio of 3-(1,2,3,6-tetrahydropyridin-2-yl)pyridine to glutarate.
3. The compound according to embodiment 1 or 2, wherein the 3-[1,2,3,6-tetrahydropyridin-2-yl]pyridine is 3-[(2S)-1,2,3,6-tetrahydropyridin-2-yl]pyridine.
4. The compound according to embodiment 1, wherein the 3-[1,2,3,6-tetrahydropyridin-2-yl]pyridine glutarate has the following formula (I):

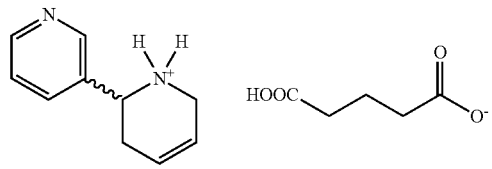 [SMILES: C1=CCC(c2cccnc2)[NH2+]C1 ; O=C([O-])CCCC(=O)O]

5. The compound according to any one of embodiments 1 to 4, wherein the 3-[1,2,3,6-tetrahydropyridin-2-yl]pyridine glutarate has the following formula (Ia):

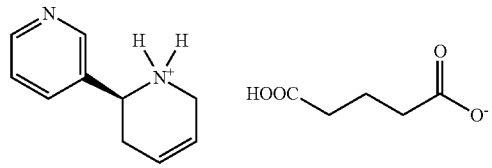 [SMILES: C1=CC[C@@H](c2cccnc2)[NH2+]C1 ; O=C([O-])CCCC(=O)O]

6. A crystal of the compound according to any one of embodiments 1 to 5.
7. A polymorphic form of the compound according to any one of embodiments 1 to 5 or the crystal according to embodiment 6.
8. The polymorphic form according to embodiment 7, wherein the polymorphic form has an X-ray powder diffraction pattern (CuKα) substantially as shown in FIG. 1.
9. The polymorphic form according to embodiment 7 or 8, wherein the polymorphic form has an X-ray powder diffraction pattern (CuKα) comprising one or more peaks selected from 8.0±0.2 °2θ, 11.0±0.2 °2θ, 13.3±0.2 °2θ, 16.5±0.2 °2θ, 18.0±0.2 °2θ, 20.7±0.2 °2θ, 21.0±0.2 °2θ, 21.4±0.2 °2θ, 22.0±0.2 °2θ, 22.3±0.2 °2θ, 23.3±0.2 °2θ and 24.5±0.2 °2θ.
10. The compound according to any one of embodiments 1 to 5, the crystal according to embodiment 6 or the polymorphic form according to any one of embodiments 7 to 9 for use as a medicament.
11. The compound according to any one of embodiments 1 to 5, the crystal according to embodiment 6 or the polymorphic form according to any one of embodiments 7 to 9, for use in the treatment or prophylaxis of substance addiction or inflammation.

12. A pharmaceutical composition for use in the treatment or prophylaxis of substance addiction or inflammation, said composition comprising a pharmaceutically effective amount of one or more of the compounds according to any one of embodiments 1 to 5, a crystal according to embodiment 6 or a polymorphic form according to any one of embodiments 7 to 9, optionally together with one or more pharmaceutically acceptable excipients.

13. A method for treating or preventing substance addiction or inflammation in a human or non-human animal patient in need thereof, wherein the method comprises administering to said patient a therapeutic effective amount of at least one compound according to any one of embodiments 1 to 5, a crystal according to embodiment 6, a polymorphic form according to any one of embodiments 7 to 9 or a pharmaceutical composition according to embodiment 12.

14. A method for preparing the compound according to any one of embodiments 1 to 5, a crystal according to embodiment 6 or a polymorphic form according to any one of embodiments 7 to 9, comprising the steps of:
preparing a solution comprising 3-[1,2,3,6-tetrahydropyridin-2-yl]pyridine, glutaric acid and a solvent,
allowing the formation of a salt of 3-[1,2,3,6-tetrahydropyridin-2-yl]pyridine with the glutaric acid, and
recovering the 3-[1,2,3,6-tetrahydropyridin-2-yl]pyridine glutaric acid salt.

15. The method according to embodiment 14, wherein the solvent used in the preparation of the solution of 3-[1,2,3,6-tetrahydropyridin-2-yl]pyridine, glutaric acid and a solvent comprises 2-methyltetrahydrofuran, acetonitrile and/or ethyl acetate.

16. The compound according to any one of embodiments 1 to 5, the crystal according to embodiment 6, the polymorphic form according to any one of embodiments 7 to 9 for use according to embodiment 11, or the pharmaceutical composition for use according to embodiment 12, wherein the substance is selected from the group consisting of nicotine, cocaine, heroine, marijuana, and alcohol.

17. The compound according to any one of embodiments 1 to 5, the crystal according to embodiment 6, the polymorphic form according to any one of embodiments 7 to 9, for use according to embodiment 11, or the pharmaceutical composition for use according to embodiment 12, wherein the inflammation is selected from the group consisting of Alzheimer's disease, thyroiditis, and multiple sclerosis.

18. The compound according to any one of embodiments 1 to 5, the crystal according to embodiment 6, the polymorphic form according to any one of embodiments 7 to 9, for use according to embodiment 11, or the pharmaceutical composition for use according to embodiment 12, in a dry powder inhaler.

19. The compound according to any one of embodiments 1 to 5, the crystal according to embodiment 6, the polymorphic form according to any one of embodiments 7 to 9, for use according to embodiment 11, or the pharmaceutical composition for use according to embodiment 12, in a thermal vaporization aerosol device.

DETAILED DESCRIPTION OF THE INVENTION

Figure 1:
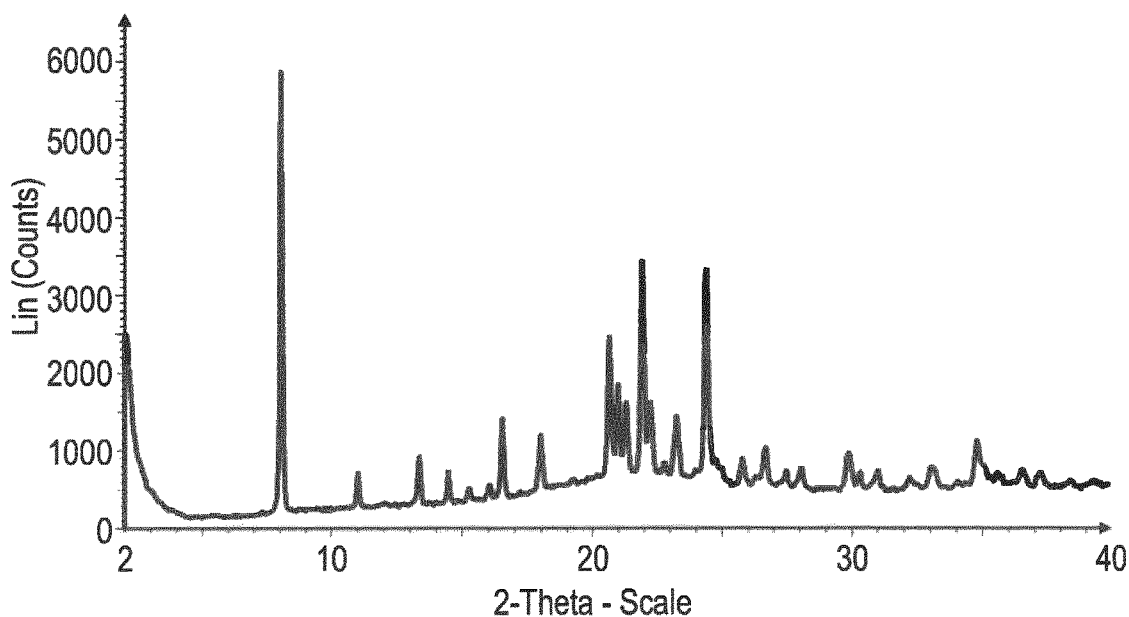
FIG. 1: X-ray powder diffraction pattern (CuKα) of the preferred polymorph of anatabine glutarate

The present invention relates to anatabine glutarate to treat disorders comprising an inflammatory component, including chronic, low-level inflammation. Anatabine is an alkaloid present in tobacco and, in lower concentrations, in a variety of foods, including green tomatoes, green potatoes, ripe red peppers, tomatillos, and sundried tomatoes. It is a main active component of the marketed dietary supplement anatabloc providing anti-inflammatory support, as disclosed in U.S. Pat. No. 9,387,201 and WO 2013/032558. The preparation of isolated forms of anatabine is described in WO 2011/119722 as well as in the following references Ref-1 to Ref-11.

Ref-1: Rossi, F. V.; Ballini, R.; Barboni, L.; Allegrini, P.; Palmieri, A. A practical and efficient synthesis of (±)-anatabine. Synthesis 2018, 50(9), 1921-1925.

Ref-2: Puthiaparampil, T. T.; David, T. K.; Raju, M. S. Methods of synthesizing anatabine. U.S. Pat. No. 8,207,346.

Ref-3: Puthiaparampil, T. T.; David, T. K.; Raju, M. S. Pharmaceutical, dietary supplement, and food grade salts of anatabine. U.S. Pat. No. 8,557,999.

Ref-4: Saloranta, T.; Leino, R. From building block to natural products: a short synthesis and complete NMR spectroscopic characterization of (±)-anatabine and (±)-anabasine. Tetrahedron Letters 2011, 52(36), 4619-4621.

Ref-5: Rouchaud, A.; Kem, W. R. A convenient racemic synthesis of two isomeric tetrahydropyridyl alkaloids: isoanatabine and anatabine. Journal of Heterocyclic Chemistry 2010, 47(3), 569-581.

Ref-6: Ayers, J. T.; Xu, R.; Dwoskin, L. P.; Crooks, P. A. A general procedure for the enantioselective synthesis of the minor Tobacco alkaloids nornicotine, anabasine, and anatabine. The AAPS Journal 2005; 7(3), Article 75.

Ref-7: Felpin, F.-X.; Vo-Thanh, G.; Robins, R. J.; Villieras, J.; Lebreton, J. Total synthesis of (S)-anabasine and (S)-anatabine. Synlett 2000, (11), 1646-1648.

Ref-8: Yang, C.-M.; Tanner, D. D. A simple synthesis of (f)-1,2,3,6-tetrahydro-2,3'-bipyridine (anatabine) and (f)-3-(2-piperidinyl)pyridine (anabasine) from lithium aluminum hydride and pyridine. Canadian Journal of Chemistry 1997, 75(6), 616-620.

Ref-9: Deo, N. M.; Crooks, P. A. Regioselective alkylation of N-(diphenylmethylidine)-3-(aminomethyl)pyridine: a simple route to minor tobacco alkaloids and related compounds. Tetr. Lett. 1996, 37 (8), 1137-1140.

Ref-10: Genisson, Y.; Mehmandoust, M.; Marazano, C.; Das, B. C. Chiral 1,2-dihydropyridines and 2,5-dihydropyridinium salt equivalents. Synthesis of (+)-anatabine and a chiral benzomorphane. Heterocycles 1994, 39(2), 811-818.

Ref-11: Quan, P. M.; Karns, T. K. B.; Quin, L. D. Total synthesis of dl-anatabine. Chemistry & Industry (London, United Kingdom) 1964, (36), 1553.

3-[1,2,3,6-Tetrahydropyridin-2-yl]pyridine (anatabine) exists as two enantiomers, namely R-(+)-anatabine and S-(−)-anatabine. Enantioselective syntheses of S- and R-enantiomers of anatabine are described, for example, in Ayers, J. T.; Xu, R.; Dwoskin, L. P.; Crooks, P. A. A general procedure for the enantioselective synthesis of the minor Tobacco alkaloids nornicotine, anabasine, and anatabine. The AAPS Journal 2005; 7(3) Article 75. In the present invention, anatabine can be used as a racemic mixture of its two enantiomers, as a purified form of S-(−)-anatabine, or as a purified form of R-(+)-anatabine. Unless otherwise clear from context, the term "anatabine" is used herein to refer to any of (1) a racemic mixture of anatabine (R,S) (2) a purified form of S-(−)-anatabine, or (3) a purified form of R-(+)-anatabine.

Pharmaceutically acceptable salts of anatabine are described in U.S. Pat. Nos. 8,207,346 and 8,557,999. In particular, Example 6 of U.S. Pat. No. 8,207,346 and Example 6 of U.S. Pat. No. 8,557,999 describe the preparation of anatabine tartrate and anatabine citrate by addition of tartaric acid or citric acid to a solution of anatabine in acetone. The formed solid was isolated by decantation, trituration with ether and drying under vacuum, but the yields of the salts are not reported.

Anatabine Glutarate

The present invention relates, in one embodiment, to a compound which is 3-(1,2,3,6-tetrahydropyridin-2-yl)pyridine glutarate (herein also referred to as anatabine glutarate) or a pharmaceutically acceptable solvate thereof. 3-(1,2,3,6-Tetrahydropyridin-2-yl)pyridine glutarate may also be referred to as a salt of 3-(1,2,3,6-Tetrahydropyridin-2-yl)pyridine with glutaric acid. Preferably, the 3-(1,2,3,6-tetrahydropyridin-2-yl)pyridine glutarate has a 1:1 molar ratio of 3-(1,2,3,6-tetrahydropyridin-2-yl)pyridine to glutarate.

It is to be understood that any reference to "3-(1,2,3,6-tetrahydropyridin-2-yl)pyridine glutarate" or "anatabine glutarate" herein is to be understood as also referring to any pharmaceutically acceptable solvate thereof.

More preferably, the 3-(1,2,3,6-tetrahydropyridin-2-yl)pyridine glutarate has a chemical structure represented by the following formula (I):

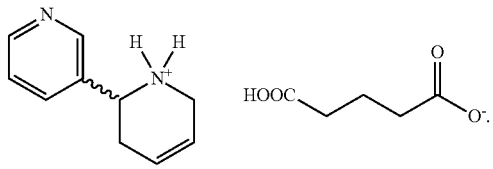

It is to be noted that 3-[1,2,3,6-tetrahydropyridin-2-yl] pyridine (anatabine) exists as two enantiomers, namely R-(+)-anatabine and S-(−)-anatabine. In the present invention, 3-[1,2,3,6-tetrahydropyridin-2-yl]pyridine is preferably 3-[(2S)-1,2,3,6-tetrahydropyridin-2-yl]pyridine.

In a preferred embodiment, the 3-[1,2,3,6-tetrahydropyridin-2-yl]pyridine glutarate may thus have the following formula (Ia):

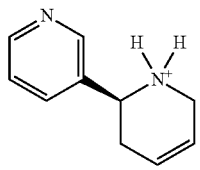 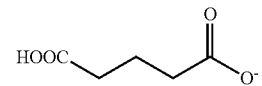

The present inventors have surprisingly found that anatabine glutarate and, to a surprisingly improved extent, the crystal and polymorph form of the crystal, have advantageous properties such as high crystallinity, morphology, thermal and mechanical stability to polymorphic conversion and/or to dehydration, storage stability, low content of residual solvent, a lower degree of hygroscopicity, flowability, and advantageous processing and handling characteristics. Furthermore, the present inventors found that anatabine glutarate recrystallizes as a crystalline salt even after having been exposed to moisture, when the moisture is removed by suitable measures, such as drying under vacuum. This finding is highly unexpected.

As can be seen from the above, the anatabine exists in the form of different isomers, in particular stereoisomers (including enantiomers and diastereomers) or tautomers. All such isomers of the anatabine glutarate are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein.

It is to be understood that any reference to 3-[1,2,3,6-tetrahydropyridin-2-yl]pyridine glutarate herein also includes any solvates and/or co-crystals thereof. solvates include any type of solvate, including, e.g., solvates with water, for example hydrates, or with organic solvents such as, e.g., methanol, ethanol or acetonitrile, i.e., as a methanolate, ethanolate or acetonitrilate, respectively, or in the form of any polymorph.

The scope of the invention also embraces 3-[1,2,3,6-tetrahydropyridin-2-yl]pyridine glutarate in which one or more atoms are replaced by a specific isotope of the corresponding atom. For example, the invention encompasses 3-[1,2,3,6-tetrahydropyridin-2-yl]pyridine glutarate, in which one or more hydrogen atoms (or, e.g., all hydrogen atoms) are replaced by deuterium atoms (i.e., 2H; also referred to as "D"). Accordingly, the invention also embraces 3-[1,2,3,6-tetrahydropyridin-2-yl]pyridine glutarate which is enriched in deuterium. Naturally occurring hydrogen is an isotopic mixture comprising about 99.98 mol-% hydrogen-1 ($^1$H) and about 0.0156 mol-% deuterium ($^2$H or D). The content of deuterium in one or more hydrogen positions in 3-[1,2,3,6-tetrahydropyridin-2-yl]pyridine glutarate can be increased using deuteration techniques known in the art. For example, a compound of formula (I) or a reactant or precursor to be used in the synthesis of 3-[1,2,3,6-tetrahydropyridin-2-yl]pyridine glutarate can be subjected to an H/D exchange reaction using, e.g., heavy water (D$_2$O). Further suitable deuteration techniques are described in: Atzrodt J et al., *Bioorg Med Chem*, 20(18), 5658-5667, 2012; William J S et al., *Journal of Labelled Compounds and Radiopharmaceuticals*, 53(11-12), 635-644, 2010; Modvig A et al., *J Org Chem*, 79, 5861-5868, 2014. The content of deuterium can be determined, e.g., using mass spectrometry or NMR spectroscopy. Unless specifically indicated otherwise, it is preferred that the 3-[1,2,3,6-tetrahydropyridin-2-yl]pyridine glutarate is not enriched in deuterium. Accordingly, the presence of naturally occurring hydrogen atoms or $^1$H hydrogen atoms in the 3-[1,2,3,6-tetrahydropyridin-2-yl]pyridine glutarate is preferred.

Methods for selectively preparing the anatabine enantiomers are described, for example, in "A General Procedure for the Enantioselective Synthesis of the Minor Tobacco Alkaloids Nornicotine, Anabasine, and Anatabine," The AAPS Journal 2005; 7(3) Article 75. Any of the methods or compositions described herein may involve providing anatabine as a racemic mixture of its two enantiomers, as a purified form of S-(−)-anatabine, or as a purified form of R-(+)-anatabine. Unless otherwise clear from context, the term "anatabine" is used herein to refer to any of (1) a racemic mixture of anatabine (R,S) (2) a purified form of S-(−)-anatabine, or (3) a purified form of R-(+)-anatabine.

The present invention furthermore relates to a crystal of 3-(1,2,3,6-tetrahydropyridin-2-yl)pyridine glutarate. The crystal is not particularly limited and may have any morphology.

The present invention furthermore relates to a specific polymorph (herein also referred to as polymorphic form) of the 3-(1,2,3,6-tetrahydropyridin-2-yl)pyridine glutarate and in particular of the crystal of the 3-(1,2,3,6-tetrahydropyridin-2-yl)pyridine glutarate. The polymorph preferably has an X-ray powder diffraction pattern (CuKα) substantially as shown in FIG. 1. The polymorph preferably has an X-ray powder diffraction pattern (CuKα) comprising one or more peaks selected from 8.0±0.2 °2θ, 11.0±0.2 °2θ, 13.3±0.2 °2θ, 16.5±0.2 °2θ, 18.0±0.2 °2θ, 20.7±0.2 °2θ, 21.0±0.2 °2θ, 21.4±0.2 °2θ, 22.0±0.2 °2θ, 22.3±0.2 °2θ, 23.3±0.2 °2θ and 24.5±0.2 °2θ. More preferably, the polymorph preferably has an X-ray powder diffraction pattern (CuKα) comprising one or more peaks selected from 8.0±0.2 °2θ, 13.3±0.2 °2θ, 16.5±0.2 °2θ, 21.4±0.2 °2θ, 22.0±0.2 °2θ and 24.5±0.2 °2θ.

Still more preferably, the polymorph preferably has an X-ray powder diffraction pattern (CuKα) comprising one or more peaks selected from 8.0±0.1 °2θ, 11.0±0.1 °2θ, 13.3±0.1 °2θ, 16.5±0.1 °2θ, 18.0±0.1 °2θ, 20.7±0.1 °2θ, 21.0±0.1 °2θ, 21.4±0.1 °2θ, 22.0±0.1 °2θ, 22.3±0.1 °2θ, 23.3±0.1 °2θ and 24.5±0.1 °2θ. Even more preferably, the polymorph preferably has an X-ray powder diffraction pattern (CuKα) comprising one or more peaks selected from 8.0±0.1 °2θ, 13.3±0.1 °2θ, 16.5±0.1 °2θ, 21.4±0.1 °2θ, 22.0±0.1 °2θ and 24.5±0.1 °2θ.

Even more specifically, the polymorph preferably has an X-ray powder diffraction pattern (CuKα) comprising one or more peaks selected from 7.960±0.2 °2θ, 10.907±0.2 °2θ, 13.291±0.2 °2θ, 14.413±0.2 °2θ, 15.239±0.2 °2θ, 16.479±0.2 °2θ, 17.933±0.2 °2θ, 20.610±0.2 °2θ, 20.977±0.2 °2θ, 21.318±0.2 °2θ, 21.927±0.2 °2θ, 22.203±0.2 °2θ, 22.792±0.2 °2θ, 23.246±0.2 °2θ, 24.426±0.2±°2θ and 24.769±0.2 °2θ. Still more specifically, the polymorph preferably has an X-ray powder diffraction pattern (CuKα) comprising one or more peaks selected from 7.960±0.1 °2θ, 10.907±0.1 °2θ, 13.291±0.1 °2θ, 14.413±0.1 °2θ, 15.239±0.1 °2θ, 16.479±0.1 °2θ, 17.933±0.1 °2θ, 20.610±0.1 °2θ, 20.977±0.1 °2θ, 21.318±0.1 °2θ, 21.927±0.1 °2θ, 22.203±0.1 °2θ, 22.792±0.1 °2θ, 23.246±0.1 °2θ, 24.426±0.1 °2θ and 24.769±0.1 °2θ.

Ion chromatography analysis has been used to confirm the presence of glutarate in a ratio 1:1 of anatabine:glutarate. The experimental examples show that anatabine glutarate is very stable and has not shown evidence of degradation under the accelerated conditions (40° C./75% RH) after 7 days. The provided data further shows that anatabine glutarate can be prepared in a single crystalline form with distinct crystal structure and physical properties, like melting point, X-ray diffraction pattern, infrared absorption fingerprint.

Polymorph screening has led to the creation of no novel polymorphic forms of the anatabine glutarate. This was further confirmed by scanning electron microscopy and comparison of DSC and XRPD patterns of samples which had been maturated in ethyl acetate and acetonitrile. Thermal properties of anatabine glutarate were determined by thermogravimetric analysis (TGA) and differential scanning calorimetry (DSC), which was used to distinguish the crystal form.

Figure 13:
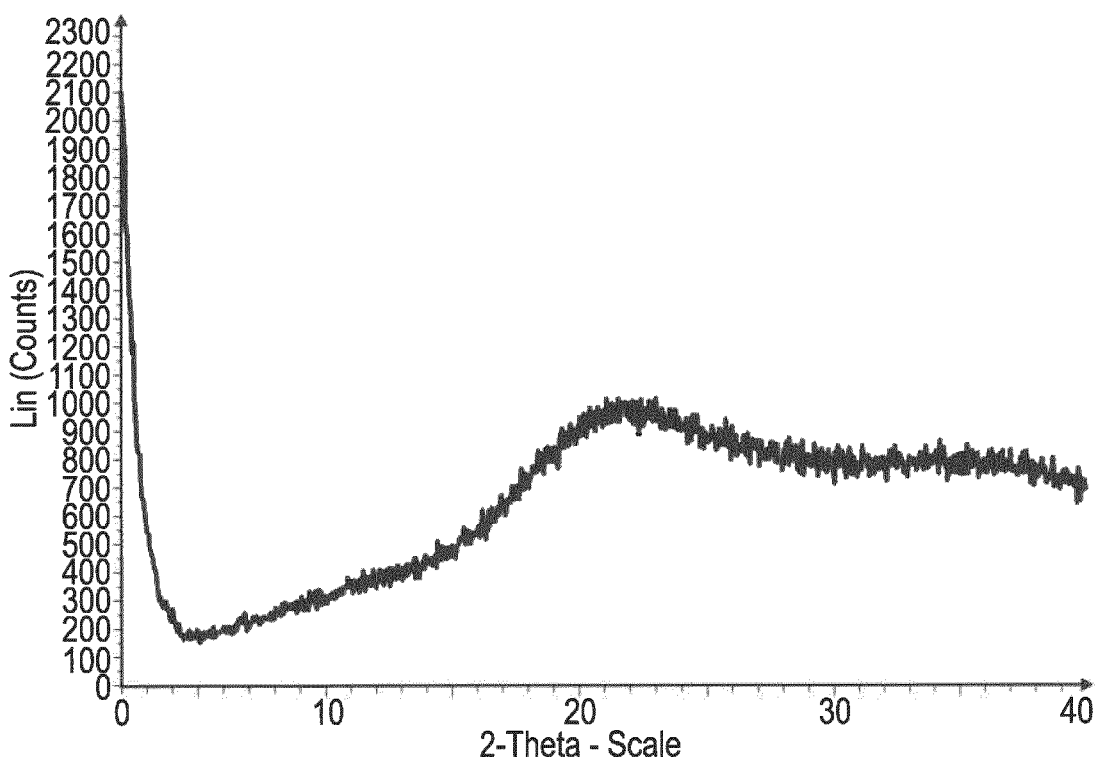
FIG. 13: XRPD diffraction pattern of anatabine tartrate
Figure 14:
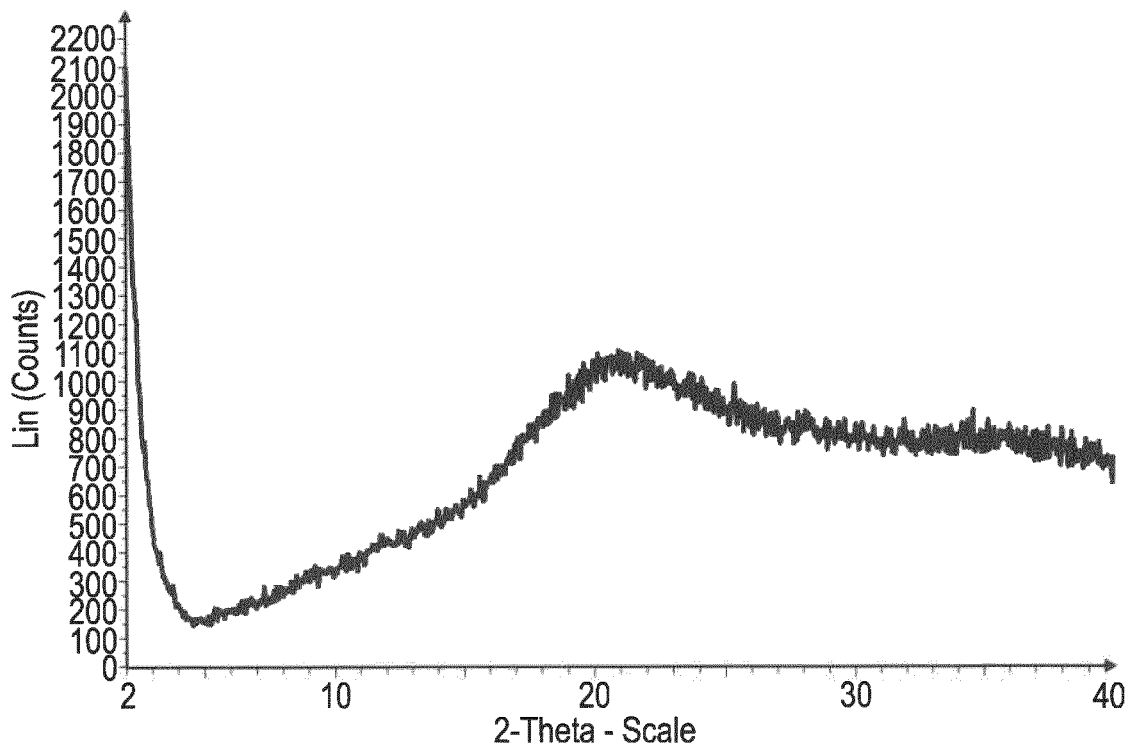
FIG. 14: XRPD diffraction pattern of anatabine citrate

Unlike the glutarate, the tartrate (FIG. 13) and the citrate (FIG. 14) have amorphous form. The citrate and the tartrate are highly hygroscopic which makes it difficult and challenging to handle it especially in large scale production and formulation. Moreover, process of preparation of the citrate which is disclosed in U.S. Pat. Nos. 8,207,346 and 8,557,999 includes precipitation from acetone. As a result, solid forms of the citrate contain captured acetone which is difficult to remove without conversion of solid into foam/gum.

The present invention also relates to a method of preparing the 3-(1,2,3,6-tetrahydropyridin-2-yl)pyridine glutarate and in particular of the crystal of the 3-(1,2,3,6-tetrahydropyridin-2-yl)pyridine glutarate.

This method comprises the steps of
  a) preparing a solution comprising 3-[1,2,3,6-tetrahydropyridin-2-yl]pyridine, glutaric acid and a solvent,
  b) allowing the formation of a salt of 3-[1,2,3,6-tetrahydropyridin-2-yl]pyridine with the glutaric acid, and
  c) recovering the 3-[1,2,3,6-tetrahydropyridin-2-yl]pyridine glutaric acid salt.

The solvent used in the preparation of the solution of 3-[1,2,3,6-tetrahydropyridin-2-yl]pyridine, glutaric acid and a solvent preferably comprises 2-methyltetrahydrofuran, acetonitrile and/or ethyl acetate. More preferably, the solvent comprises 2-methyltetrahydrofuran.

The method may furthermore comprise a step of d) recrystallizing the 3-[1,2,3,6-tetrahydropyridin-2-yl]pyridine glutaric acid salt. Suitable solvents for this recrystallization include acetonitrile.

In step a), the anatabine glutarate can be prepared by combining anatabine free base, a solvent, and glutaric acid to create a reaction mixture. Anatabine glutarate typically forms in such a reaction mixture through contact of anatabine free base with glutaric acid. Preferably, anatabine free base as a 1 to 5 mass-% solution in acetonitrile is combined with glutaric acid.

Preferably a solution or suspension of anatabine free base, a solvent and glutaric acid is combined to form a reaction mixture, followed by precipitation and recovery of the anatabine glutarate salt from the mixture. Glutaric acid may be added either as a solid or as a solution or a suspension in a solvent.

The solvent is preferably selected from the group consisting of alkanols containing 1 to 8 carbon atoms, aliphatic esters containing 3 to 8 carbon atoms, aliphatic linear or cyclic ethers containing 3 to 8 carbon atoms, aliphatic ketones containing 3 to 8 carbon atoms, $C_{6-12}$ aromatic hydrocarbons (such as benzene and napthalene), acetonitrile, water, and any mixtures thereof. Preferably, the solvent is selected from aliphatic esters containing 3 to 8 carbon atoms, aliphatic cyclic ethers containing 3 to 8 carbon atoms, acetonitrile and a mixture thereof. More preferably, the solvent is selected from ethyl acetate, acetonitrile, 2-methyltetrahydrofuran, and any mixtures thereof. Even more preferably, the solvent contains acetonitrile. Still more preferably, the solvent is acetonitrile.

The anatabine free base, glutaric acid, and the at least one solvent are preferably combined to form the reaction mixture at about room temperature (i.e. a range of preferably 15° C. to 25° C.). The concentration of glutaric acid present in such reaction mixture is preferably a concentration close to the point of saturation (e.g. at least 80%, preferably 90%, more preferably 95% of the maximum achievable concentration). Anatabine glutarate typically precipitates out of the mixture. The precipitation may occur on its own or be induced, e.g., by the introduction of seed crystals. The reaction mixture may be stirred before, during, or after precipitation.

The reaction mixture may be heated and then cooled to facilitate precipitation of anatabine glutarate. Heating may be carried out up to any temperature (e.g. about 50° C. to about 80° C.) in the range of from room temperature to the boiling temperature of the solvent. Thereafter, cooling is generally conducted down to less than 40° C., preferably about 30° C. to about 20° C., more preferably room temperature (i.e. a range of preferably 15° C. to 25° C.), to facilitate precipitation.

The resulting precipitate may be recovered by various techniques, such as filtration. The precipitate may be dried under ambient or reduced pressure and/or elevated temperature.

Medical Uses

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than 0, often are greater than about 0.1, and frequently are greater than about 0.5. The log P values of such typical compounds generally are less than about 3.0, often are less than about 2.5, and frequently are less than about 2.0. Log P values provide a measure of the ability of a compound to pass across a diffusion barrier, such as a biological membrane. See, Hansch, et al., J. Med. Chem., Vol. 11, p. 1 (1968).

The compounds useful according to the method of the present invention have the ability to bind to, and hence cause activation of, nicotinic cholinergic receptors of the brain of the patient. As such, such compounds have the ability to act as nicotinic agonists. The receptor binding constants of typical compounds useful in carrying out the present invention generally exceed about 1 nM, often exceed about 200 nM, and frequently exceed about 500 nM. The receptor binding constants of such typical compounds generally are less than about 10 µM, often are less than about 7 µM, and frequently are less than about 2 µM. Receptor binding constants provide a measure of the ability of the compound to bind to half of the relevant receptor sites of certain brain cells of the patient. See, Cheng, et al., Biochem. Pharmacol., Vol. 22, pp. 3099-3108 (1973).

The compounds useful according to the method of the present invention have the ability to demonstrate a nicotinic function by effectively eliciting neurotransmitter secretion from nerve ending preparations (i.e., synaptosomes). As such, such compounds have the ability to cause relevant neurons to release or secrete acetylcholine, dopamine, and other neurotransmitters.

Generally, typical compounds useful in carrying out the present invention provide for the secretion of dopamine in amounts of at least about 3 percent, often at least about 25 percent, and frequently at least about 50 percent, of that elicited by an equal molar amount of (s)-(–)-nicotine.

Thus, the present invention encompasses the compounds, the crystal or the polymorphic form described herein for use as a medicament. The medicament is preferably for use in the treatment or prophylaxis of substance addiction or inflammation. A method for treating or preventing nicotine addiction or inflammation in a human or non-human animal patient in need thereof is also part of the present invention. The present invention further relates to a pharmaceutical composition for use in the treatment or prophylaxis of substance addiction or inflammation, said composition comprising a pharmaceutically effective amount of one or more of the compounds, crystals or polymorphic forms described herein, optionally together with one or more pharmaceutically acceptable excipients.

The "human or non-human animal patient" as used herein includes warm-blooded animals, typically mammals, including humans and other primates. In some embodiments the patient is an animal, such as a companion animal, a service animal, a farm animal, or a zoo animal. Such animals include, but are not limited to, canines (including dogs, wolves), felines (including domestic cats, tigers, lions), ferrets, rabbits, rodents (e.g., rats, mice), guinea pigs, hamsters, gerbils, horses, cows, pigs, sheep, goats, giraffes, and elephants. Thus, the anatabine glutarate as disclosed herein can be used in both human therapy and veterinary applications.

In some embodiments an isolated form of anatabine glutarate can be administered to reduce the risk of developing a disorder comprising an NFKB-mediated inflammatory component (i.e., prophylactically). One can readily identify individuals with an increased risk or family history of such a disorder. Other recognized indices of elevated risk of certain disorders can be determined by standard clinical tests or medical history.

In some embodiments an isolated form of anatabine glutarate can be administered to reduce the risk of developing a disorder comprising a STAT3-mediated inflammatory component (i.e., prophylactically). One can readily identify individuals with an increased risk or family history of such a disorder. Other recognized indices of elevated risk of certain disorders can be determined by standard clinical tests or medical history.

The inflammation is preferably selected from the group consisting of Alzheimer's disease, thyroiditis, and multiple sclerosis. However, the range of disorders that may be treated with the compound, crystal, polymorphic form or pharmaceutical composition is much broader and will be set out in the following:

thyroiditis,
an immune or autoimmune disorder,
arthritis, such as rheumatoid arthritis, primary and secondary osteoarthritis (also known as degenerative joint disease),
a spondyloarthropathy, such as psoriatic arthritis, juvenile chronic arthritis with late pannus onset, and enterogenic spondyloarthropathies such as enterogenic reactive arthritis, urogenital spondyloarthropathy, and undifferentiated spondylarthropathy, a myopathy, such as "soft tissue rheumatism" (e.g., tennis elbow, frozen shoulder, carpal tunnel syndrome, plantar fasciitis, and Achilles tendonitis), diabetes, either type I diabetes or type II diabetes, a gastrointestinal inflammatory disorder, such as an inflammatory bowel disease, e.g., Crohn's disease, Barrett's syndrome, ileitis, irritable bowel syndrome, irritable colon syndrome, ulcerative colitis, pseudomembranous colitis, hemorrhagic colitis, hemolytic-uremic syndrome colitis, collagenous colitis, ischemic colitis, radiation colitis, drug and chemically induced colitis, diversion colitis, colitis in conditions such as chronic granulomatous disease, celiac disease, celiac sprue, food allergies, gastritis, infectious gastritis, enterocolitis (e.g., *Helicobacter pylori*-infected chronic active gastritis), and pouchitis, graft-versus-host-disease (GVHD), systemic lupus erythematosus (SLE), lupus nephritis, Addison's disease, Myasthenia gravis, vasculitis (e.g., Wegener's granulomatosis), autoimmune hepatitis, osteoporosis, and some types of infertility, vascular inflammatory disease, associated vascular pathologies, atherosclerosis, angiopathy, inflammation-induced atherosclerotic or thromboembolic macroangiopathy, coronary artery disease, cerebrovascular disease, peripheral vascular disease, cardiovascular circulatory disease such as ischemia/reperfusion, peripheral vascular disease, restenosis following angioplasty, inflammatory aortic aneurysm, vasculitis, stroke, spinal cord injury, congestive heart failure, hemorrhagic shock, ischemic heart disease/reperfusion injury, vasospasm following subarachnoid hemorrhage, vasospasm following cerebrovascular accident, pleuritis, pericarditis, inflammation-induced myocarditis, or a cardiovascular complication of diabetes, brain swelling or a neurodegenerative disease such as multiple sclerosis, Alzheimer's disease, or Parkinson's disease.

inflammation related to a kidney disease, nephritis, glomerulonephritis, dialysis, peritoneal dialysis, pericarditis, chronic prostatitis, vasculitis, gout, or pancreatitis, an anemia, an ulcer-related disease, such as peptic ulcer disease, acute pancreatitis, or aphthous ulcer, related to an age-related disease, such as atherosclerosis, fibrosis, and osteoporosis, or a disorder associated with pre-maturity, such as retinopathy, chronic lung disease, arthritis, and digestive problems, preeclampsia, inflammation related to chemical or thermal trauma due to burns, acid, and alkali, chemical poisoning (MPTP/concavalin/chemical agent/pesticide poisoning), snake, spider, or other insect bites, adverse effects from drug therapy (including adverse effects from amphotericin B treatment), adverse effects from immunosuppressive therapy (e.g., interleukin-2 treatment), adverse effects from OKT3 treatment, adverse effects from GM-CSF treatment, adverse effects of cyclosporine treatment, and adverse effects of aminoglycoside treatment, stomatitis and mucositis due to immunosuppression, or exposure to ionizing radiation, such as solar ultraviolet exposure, nuclear power plant or bomb exposure, or radiation therapy exposure, such as for therapy for cancer, cancer, such as acute lymphoblastic leukemia, acute myeloid leukemia, adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast cancer, breast sarcoma, bronchial cancer, bronchoalveolar carcinoma, Burkitt lymphoma, cervical cancer, chronic lymphocytic leukemia, chronic myelogenous leukemia, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, hairy cell leukemia, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplasia/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sezary syndrome, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenstrom macroglobulinemia, or Wilms tumor, disorders associated with inflammation in the stomach and/or esophagus, such as acid reflux.

WO 2011/119722 indicates that anatabine reduces transcription mediated by nuclear factor κB (NFKB). NFKB is a transcription factor which operates in cells involved in inflammatory and immune reactions. NFKB-mediated transcription is associated with numerous disorders, including those with an inflammatory component, an aberrant immune response, and/or inappropriate cell proliferation. The claimed anatabine glutarate is particularly useful for treating disorders comprising an "NFKB-mediated inflammatory component," i.e. inflammation characterized by, caused by, resulting from, or affected by NFKB-mediated transcription. NFKB-mediated transcription is implicated in a variety of maladies. Based on anatabine glutarate's surprising efficacy in interfering with or interrupting this pivotal inflammatory-related activity, anatabine glutarate can be expected to have a wide range of therapeutic utilities. It is thus expected that the compounds, crystals, polymorphic forms and pharmaceutical compositions of the present invention will be useful in the treatment or prophylaxis of the various diseases set out above.

The compounds, crystals, polymorphic forms and/or pharmaceutical compositions of the present invention may also be used in conjunction with (i.e., before, after, or at the same time as) other therapies for any disorder with an NFKB-mediated component. In some embodiments, these therapies include other products that inhibit production of NFKB mediated inflammatory species. These products include, but are not limited to, dexamethasone, glucocorticoids (e.g., prednisone, methyl prednisolone), cyclosporine, tacrolimus, deoxyspergualin, non-steroidal antiinflammatory drugs (NSAIDs) such as aspirin and other salicylates, tepoxalin, synthetic peptide proteosome inhibitors, antioxidants (e.g., N-acetyl-L-cysteine, vitamin C, vitamin E, dithiocarbamate derivatives, curcumin), IL-10, nitric oxide, cAMP, gold-containing compounds, and gliotoxin.

The compounds, crystals, polymorphic forms and pharmaceutical compositions of the present invention may be administered to the individual at a dose sufficient to reduce a symptom of a disorder with an NFKB-mediated-transcription component.

It has also been shown, namely by Paris et al. (2013) European Journal of Pharmacology 698, 145-153, that anatabine has an anti-inflammatory activity both in the periphery and the CNS via a regulation of STAT3 and NFkB signaling. Accordingly, the compound, crystal, polymorph and/or pharmaceutical composition of the invention may in addition to NFKB or alternatively inhibit STAT3. The claimed anatabine glutarate is particularly useful for treating disorders comprising an "STAT3-mediated inflammatory component," i.e. inflammation characterized by, caused by, resulting from, or affected by STAT3-mediated transcription. STAT3-mediated transcription is implicated in a variety of maladies. Based on anatabine glutarate's surprising efficacy in interfering with or interrupting this pivotal inflammatory-related activity, anatabine glutarate can be expected to have a wide range of therapeutic utilities. It is thus expected that the compounds, crystals, polymorphic forms and pharmaceutical compositions of the present invention will be useful in the treatment or prophylaxis of the various diseases set out herein.

The compounds, crystals, polymorphic forms and/or pharmaceutical compositions of the present invention may also be used in conjunction with (i.e., before, after, or at the same time as) other therapies for any disorder with an STAT3-mediated component. In some embodiments, these therapies include other products that inhibit production of STAT3 mediated inflammatory species. In a particular embodiment, the compound, crystal, polymorph and/or pharmaceutical composition of the invention has both a STAT3 and NFKB inhibitory effect.

The compounds, crystals, polymorphic forms and pharmaceutical compositions of the present invention may be administered to the individual at a dose sufficient to reduce a symptom of a disorder with a STAT3-mediated-transcription component.

In another embodiment of the present invention an isolated form of anatabine glutarate may be administered to prevent or treat substance addiction. Anatabine glutarate may be administered to individuals suffering from substance addiction to overcome the addiction. Anatabine glutarate may also be administered to individuals that have overcome substance addiction to prevent them from relapsing. Anatabine glutarate may further be administered to individuals not suffering from substance addiction to prevent them from substance addiction. The substance of the substance addiction is preferably selected from the group consisting of nicotine, cocaine, heroine, marijuana, and alcohol.

WO 2012/2005885 indicates that compositions containing anatabine are efficacious for temporally reducing the desire to smoke, reducing nicotine cravings, the treatment of smoking cessation, tobacco withdrawal symptoms, tobacco dependence, weight loss and/or related disorders, even without the presence of nicotine. Anatabine and other minor alkaloids also have been reported to bind to nicotinic receptors. WO2015/009500 further indicates that anatabine may activate human nicotinic acetylcholine receptors, but very high concentrations beyond any recommended or tolerated doses are likely needed to produce significant agonist effects. This suggestion is supported by behavioral data which showed that rodents trained to self-administer nicotine do not find anatabine to be rewarding, and that anatabine administration does not reverse precipitated nicotine withdrawal. The present invention is based on the surprising finding that anatabine glutarate is particularly efficacious in this respect. Moreover, specific crystalline/polymorphic forms as provided herein are particularly efficacious.

In a further embodiment, the present invention provides a method of treating certain medical, psychiatric and/or neurological conditions or disorders. In one embodiment of the invention, the method comprises administering a MAO-inhibiting effective amount of the compound, the crystal, the polymorph and/or the pharmaceutical composition of the invention to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a further embodiment of the invention, the method comprises administering a MAO-inhibiting effective amount of the compound, the crystal, the polymorph and/or the pharmaceutical composition of the invention to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a further embodiment of the invention, the method comprises administering a MAO-inhibiting effective amount of the compound, the crystal, the polymorph and/or the pharmaceutical composition of the invention to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and *cannabis* (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a further embodiment of the invention, the method comprises administering a MAO-inhibiting effective amount of the compound, the crystal, the polymorph and/or the pharmaceutical composition of the invention in the form of a gum and lozenges formulated therewith to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a yet further embodiment, the compound, the crystal, the polymorph and/or the pharmaceutical composition of the invention may be administered to treat/prevent a disorder or disease of the group of autism spectrum disorders (ASDs). Autism spectrum disorders (ASDs) are pervasive neurodevelopmental disorders diagnosed in early childhood when acquired skills are lost or the acquisition of new skills becomes delayed. ASDs onset in early childhood and are associated with varying degrees of dysfunctional communication and social skills, in addition to repetitive and stereotypic behaviors. In many cases (25%-50%), a period of seemingly normal development drastically shifts directions as acquired skills are lost or the acquisition of new skills becomes delayed. Examples of Autism Spectrum Disorders include "classical" autism, Asperger's syndrome, Rett syndrome, childhood disintegrative disorder, and atypical autism otherwise known as pervasive developmental disorder not otherwise specified (PDD-NOS).

Autism is a childhood psychosis originating in infancy and characterized by a wide spectrum of psychological symptoms that progress with age (eg, lack of responsiveness in social relationships, language abnormality, and a need for constant environmental input). It generally appears in children between the ages of two and three years and gives rise to a loss of the development previously gained by the child. Autistic individuals are at increased risk of developing seizure disorders, such as epilepsy.

Excess inflammation has been found in the colon, esophagus, and duodenum of patients with autism, and postmortem studies have also shown an increase in the expression of several markers for neuroinflammation (see Table 1). Proinflammatory cytokines, including TNFα and IL-1, are overproduced in a subset of autistic patients, indicating that these patients had excessive innate immune responses and/or aberrant production of regulatory cytokines for T cell responses (eg, 20030148955. Isolated forms of anatabine, including S-(−)-anatabine, or salts of such isolated forms are particularly useful for treating disorders comprising an "NFκB-mediated inflammatory component," i.e. inflammation characterized by, caused by, resulting from, or affected by NFκB-mediated transcription. Thus, a compound of Formula I (e g, anatabine or S-(−)-anatabine or a pharmaceutically acceptable salt thereof) in isolated form may be useful in treating or reducing a symptom of an ASD. Use of isolated forms of the compound, the crystal, the polymorph and/or the pharmaceutical composition of the invention avoids the toxicity associated with tobacco, tobacco extracts, alkaloid extracts, and nicotine.

Neuroinflammation is a well-established response to central nervous system injury (Minghetti, Curr Opin Neurol 2005; 18:315-21). Human pathologic, in vitro, and in vivo studies of Alzheimer's disease have implicated a glia-mediated neuroinflammatory response both in the pathophysiology of the disease (Mrak & Griffin, Neurobiol Aging 26:349-54, 2005) and as treatment target (Hu et al., Bioorgan Med Chem Lett 17:414-18, 2007; Ralay et al, J Neurosci 26:662-70, 2006; Crafl et al., Exp Opin Therap Targets 9:887-900, 2005). Microglial activation leading to overexpression of IL-1 has been proposed as the pivotal step in initiating a self propagating cytokine cycle culminating in neurodegeneration (Mrak & Griffin, Neurobiol Aging 26:349-54, 2005; Sheng el al., Neurobiol Aging 17:761-66. 1996). IL-1β and pro-inflammatory cytokines may function in epilepsy as pro-convulsant signaling molecules independent of such a cycle (Vezzani et al., Epilepsia 43:530-S35, 2002), which provides a potential therapeutic target in epilepsy and other seizure disorders (Vezzani & Granata, Epilepsia 46: 1724-43, 2005)

In some embodiments an isolated form of the compound, the crystal, the polymorph and/or the pharmaceutical composition of the invention is administered to treat seizures, including the generalized and partial seizures.

As described in The Pharmacological Basis of Therapeutics, 9th ed., (McGraw-Hill), there are two classes of seizures: partial seizures and generalized seizures. Partial seizures consist of focal and local seizures. Partial seizures are further classified as simple partial seizures, complex partial seizures and partial seizures secondarily generalized. Generalized seizures are classified as convulsive and nonconvulsive seizures. They are further classified as absence (previously referred to as petit mal) seizures, atypical absence seizures, myoclonic seizures, clonic seizures, tonic seizures, tonic-clonic seizures, and atonic seizures.

Generalized seizures include infantile spasms, absence seizures, tonic-clonic seizures, atonic seizures, and myoclonic seizures. Abnormal motor function and a loss of consciousness are major features of these seizures. A patient may also experience an aura of sensory, autonomic, or psychic sensations. The aura may include paresthesia, a rising epigastric sensation, an abnormal smell, a sensation of fear, or a dejavu sensation. A generalized seizure is often followed by a postictal state, in which a patient may sleep deeply, be confused, and/or have a headache or muscle ache. Todd's paralysis (limb weakness contralateral to the seizure focus) may be present in the postictal state.

Infantile spasms are characterized by frequent flexion and adduction of the arms and forward flexion of the trunk, usually of short duration. They occur only in the first 5 years of life.

Typical absence seizures (also known as petit mal seizures) are characterized by a loss of consciousness with eyelid fluttering, typically for 10-30 seconds or more. There may or may not be a loss of axial muscle tone. Convulsions are absent; instead, patients abruptly stop activity, then abruptly resume it, often without realizing that a seizure has occurred. Absence seizures are genetic. They occur predominantly in children, often frequently throughout the day.

Atypical absence seizures occur as part of the Lennox-Gastaut syndrome, a severe form of epilepsy. They last longer than typical absence seizures and jerking or automatic movements are more pronounced.

Atonic seizures occur most often in children, usually as part of Lennox-Gastaut syndrome. They are characterized by a complete loss of muscle tone and consciousness.

Tonic seizures also occur most often in children, usually as part of Lennox-Gastaut syndrome. They are characterized by tonic (sustained) contraction of axial and proximal muscles, usually during sleep, and last 10 to 15 seconds. In longer tonic seizures a few, rapid clonic jerks may occur at the end of the seizure.

Tonic-clonic seizures, also known as grand mal seizures, may be primarily or secondarily generalized. A patient experiencing a primarily generalized tonic-clonic seizure will often cry out, then lose consciousness and fall. Tonic contractions then begin, followed by clonic (rapidly alternating contraction and relaxation) motion of muscles of the extremities, trunk, and head. A patient may lose urinary and fecal continence, bite his tongue, and froth at the mouth. Seizures usually last 1 to 2 min. There is no aura. Secondarily generalized tonic-clonic seizures begin with a simple partial or complex partial seizure, and then progress to a generalized seizure.

Myoclonic seizures are characterized by brief, rapid jerks of a limb, several limbs, or the trunk. They may be repetitive, leading to a tonic-clonic seizure. The jerks may be bilateral or unilateral. Consciousness is not lost unless the seizures progress into a generalized tonic-clonic seizure.

Juvenile myoclonic epilepsy is an epilepsy syndrome characterized by myoclonic, tonic-clonic, and absence seizures. Patients are usually adolescents. Seizures typically begin with bilateral, synchronous myoclonic jerks, followed in 90% by generalized tonic-clonic seizures. They often occur on rising in the morning. A third of patients may experience absence seizures.

Febrile seizures are associated with fever, but not intracranial infection. Benign febrile seizures are characterized by generalized tonic-clonic seizures of brief duration. Such seizures are common in children, affecting up to four percent of children younger than six years of age. Complicated febrile seizures are characterized by focal seizures lasting more than fifteen minutes or occurring more than twice in twenty four hours. Two percent of children with febrile seizures develop a subsequent seizure disorder. The risk is greater in children with complicated febrile seizures, preexisting neurologic abnormalities, onset before age 1 yr, or a family history of seizure disorders.

Status epilepticus is a seizure disorder characterized by tonic-clonic seizure activity lasting more than five to ten minutes, or two or more seizures between which patients do not fully regain consciousness. If untreated, seizures lasting more than sixty minutes may cause brain damage or death.

Complex partial status epilepticus and absence status epilepticus are characterized by prolonged episodes of mental status changes. Generalized convulsive status epilepticus may be associated with abrupt withdrawal of anticonvulsants or head trauma.

Simple partial seizures are characterized by motor, sensory, or psychomotor symptoms without loss of consciousness. Seizures in different parts of the brain often produce distinct symptoms.

An aura often precedes complex partial seizures. Patients are usually aware of their environment but may experience impaired consciousness. Patients may also experience oral automatisms (involuntary chewing or lip smacking), hand or limb automatisms (automatic purposeless movements), utterance of unintelligible sounds, tonic or dystonic posturing of the extremity contralateral to the seizure focus, head and eye deviation, usually in a direction contralateral to the seizure focus, and bicycling or pedaling movements of the legs, especially where the seizure emanates from the medial frontal or orbitofrontal head regions. Motor symptoms subside after one or two minutes, and confusion and disorientation one to two minutes later Postictal amnesia is common.

Epilepsy is an important example of a seizure disorder. "Epilepsy" describes a group of central nervous system disorders that are characterized by recurrent seizures that are the outward manifestation of excessive and/or hyper-synchronous abnormal electrical activity of neurons of the cerebral cortex and other regions of the brain. This abnormal electrical activity can be manifested as motor, convulsion, sensory, autonomic, or psychic symptoms.

Hundreds of epileptic syndromes have been defined as disorders characterized by specific symptoms that include epileptic seizures. These include, but are not limited to, absence epilepsy, psychomotor epilepsy, temporal lobe epilepsy, frontal lobe epilepsy, occipital lobe epilepsy, parietal lobe epilepsy, Lennox-Gastaut syndrome, Rasmussen's encephalitis, childhood absence epilepsy, Ramsay Hunt Syndrome type I, benign epilepsy syndrome, benign infantile encephalopathy, benign neonatal convulsions, early myoclonic encephalopathy, progressive epilepsy and infantile epilepsy A patient may suffer from any combination of different types of seizures. Partial seizures are the most common, and account for approximately 60% of all seizure types.

Examples of generalized seizures which may be treated include infantile spasms, typical absence seizures, atypical absence seizures, atonic seizures, tonic seizures, tonic-clonic seizures, myoclonic seizures, and febrile seizures. Examples of partial seizures which may be treated include simple partial seizures affecting the frontal lobe, contralateral frontal lobe, supplementary motor cortex, the insula, the Insular-orbital-frontal cortex, the anteromedial temporal lobe, the amygdala (including the opercular and/or other regions), the temporal lobe, the posterior temporal lobe, the amygdala, the hippocampus, the parietal lobe (including the sensory cortex and/or other regions), the occipital lobe, and/or other regions of the brain.

In some embodiments an isolated form of the compound, the crystal, the polymorph and/or the pharmaceutical composition of the invention is administered to treat an epileptic syndrome including, but not limited to, absence epilepsy, psychomotor epilepsy, temporal lobe epilepsy, frontal lobe epilepsy, occipital lobe epilepsy, parietal lobe epilepsy, Lennox-Gastaut syndrome, Rasmussen's encephalitis, childhood absence epilepsy, Ramsay Hunt Syndrome type II, benign epilepsy syndrome, benign infantile encephalopathy, benign neonatal convulsions, early myoclonic encephalopathy, progressive epilepsy and infantile epilepsy.

An isolated form of the compound, the crystal, the polymorph and/or the pharmaceutical composition of the invention may also be useful for treating the aura that accompanies seizures. Thus, impaired consciousness, oral automatisms, hand or limb automatisms, utterance of unintelligible sounds, tonic or dystonic posturing of extremities, head and eye deviation, bicycling or pedaling movements of the legs and other symptoms that comprise the aura also may be treated.

Neonatal seizures are associated with later neurodevelopmental and cognitive deficits including mental retardation, autism, and epilepsy, and it is estimated that up to 40% of cases of autism suffer from epilepsy or have a history of or seizures earlier in life. Accordingly, important target patients are infants, particularly neonates, and persons with a personal or family a history of seizure, mental retardation or autism.

This disclosure also provides methods and compositions for treating a patient post-seizure. In one embodiment, an isolated form of the compound, the crystal, the polymorph and/or the pharmaceutical composition of the invention is administered in conjunction with a second therapeutic agent, such as a neurotransmitter receptor inhibitor (e.g., an inhibitor of an AMPA receptor, NMDA receptor GABA receptor, chloride cotransporters, or metabatropic glulamate receptor), a kinase/phosphatase inhibitor (e.g., an inhibitor of calmodulin kinase II (CamK H), protein kinase A (PKA), protein kinase C (PKC), MAP Kinase, Src kinase, ERK kinase or the phosphatase calcineurin), and/or a protein translation inhibitor.

Calmodulin kinase II (CamK I) inhibitors include KN-62, W-7, HA-1004, HA-1077, and staurosporine. Protein kinase A (PKA) inhibitors include H-89, HA-1004, H-7, H-8, HA-100, PKI, and staurosporine.

Protein kinase C (PKC) inhibitors include competitive inhibitors for the PKC ATP-binding site, including staurosporine and its bisindolylmaleimide derivitives, Ro-31-7549, Ro-31-8220, Ro-31-8425, Ro-32-0432 and Sangivamvcin; drugs which interact with the PKC's regulatory domain by competing at the binding sites of diacy Iglycerol and phorbol esters, such as calphostin C, Safingol, D-erythro-Sphingosine; drugs which target the catalytic domain of PKC, such as chelerythrine chloride, and Melittin; drugs which inhibit PKC by covalently binding to PKC upon exposure to UV lights, such as dequalinium chloride; drugs which specifically inhibit Ca-dependent PKC such as Go6976, Go6983, Go7874 and other homologs, polymy xin B sulfate; drugs comprising competitive peptides derived from PKC sequence; and [0056]PKC inhibitors such as cardiotoxins, ellagic acid, HBDDE, 1-O-Hexadecy 1-2-O-methyl-rac-glycerol, Hypercin, K-252, NGIC-1, Phloretin, piceatannol, and Tamoxifen citrate.

MAP kinase inhibitors include SB202190 and SB203580. SRC kinase inhibitors include PP1, PP2, Src Inhibitor No. 5, SU6656, and staurosporine. ERK kinase inhibitors include PD 98059, SL327, olomoucine, and 5-lodotubercidin. Calcineurin inhibitors include tacrolimus and cyclosporine.

Protein translation inhibitors include mTOR inhibitors, such as rapamycin, CCI-779 and RAD 001.

An isolated form of the compound, the crystal, the polymorph and/or the pharmaceutical composition of the invention is administered to the individual at a dose sufficient to reduce a symptom of an Autism Spectrum Disorder or at a dose sufficient to reduce a symptom of a seizure disorder. Doses typically range from about 1 µg/kg to about 7 mg/kg body weight (e.g., about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 µg/kg or about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2,1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mg/kg), about 1.5 µg/kg to about 5 µg/kg, about 1 sg/kg to about 10 µg/kg, about 0.01 mg/kg to about 7 mg/kg body weight, about 0.1 mg/kg to about 5 mg/kg; about 0.1 mg/kg to about 2 mg/kg, about 1 mg/kg to about 3 mg/kg, about 0.5 mg/kg to about 2 mg/kg, about 1 mg/kg to about 2 mg/kg, about 3 mg/kg to about 5 mg/kg, about 2 mg/kg to about 4 mg/kg, about 2 mg/kg to about 5 mg/kg, or about 0.5 mg/kg to about 1.5 mg/kg. Certain factors may influence the dose sufficient to reduce a symptom of a disorder (i.e., an effective dose), including the severity of the disease or disorder, previous treatments, the general health, age, and/or weight of the individual, the frequency of treatments, the rate of release from the composition, and other diseases present. This dose may vary according to factors such as the disease state, age, and weight of the subject. For example, higher doses may be administered for treatments involving conditions which are at an advanced stage and/or life-threatening. Dosage regimens also may be adjusted to provide the optimum therapeutic response.

In some embodiments the dose sufficient to reduce the symptom of the disorder can include a series of treatments. For example, an individual can be treated with a dose of an isolated form of the compound, the crystal, the polymorph and/or the pharmaceutical composition of the invention several times per day (e.g., 2-12 or 4-10 times per day), once daily, or less frequently such as 1-6 times per week. In other embodiments, the compound administered is a compound of Formula I, IA, or IB, which is administered several times per day (e.g., 2-12 or 4-10 times per day), once daily, or less frequently such as 1-6 times per week. Treatments may span between about 1 to 10 weeks (e.g., between 2 to 8 weeks, between 3 to 7 weeks, for about 1, 2, 3, 4, 5, 6, 7, 8, 9, or 10 weeks). It will also be appreciated that a dose regimen used for treatment may increase or decrease over the course of a particular treatment.

In one embodiment of the invention, anatabine glutarate is administered to a patient to treat or prevent substance addiction or inflammation. Doses typically range from about 1 µg/kg to about 7 mg/kg body weight (e.g., about 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 µg/kg or about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mg/kg), about 1.5 µg/kg to about 5 µg/kg, about 1 µg/kg to about 10 µg/kg, about 0.01 mg/kg to about 7 mg/kg body weight, about 0.1 mg/kg to about 5 mg/kg; about 0.1 mg/kg to about 2 mg/kg, about 1 mg/kg to about 3 mg/kg, about 0.5 mg/kg to about 2 mg/kg, about 1 mg/kg to about 2 mg/kg, about 3 mg/kg to about 5 mg/kg, about 2 mg/kg to about 4 mg/kg, about 2 mg/kg to about 5 mg/kg, or about 0.5 mg/kg to about 1.5 mg/kg. Certain factors may influence the dose sufficient to reduce a symptom of a disorder (i.e., an effective dose), including the severity of the disease or disorder, previous treatments, the general health, age, and/or weight of the individual, the frequency of treatments, the rate of release from the composition, and other diseases present. This dose may vary according to factors such as the disease state, age, and weight of the subject. For example, higher doses may be administered for treatments involving conditions which are at an advanced stage and/or life-threatening. Dosage regimens also may be adjusted to provide the optimum therapeutic response.

For example, tablets comprising about 600 µg anatabine glutarate are administered from once to 25 times daily (e.g., 1, 2, 3, 4, 5, 6, 7, 8, 9, 10, 11, 12, 13, 14, 15, 16, 17, 18, 19, 20, 21, 22, 23, 24, or 25) times daily.

The dose sufficient to reduce the symptom of the disorder can optionally include a series of treatments. For example, an individual can be treated with a dose of an isolated form of anatabine glutarate several times per day, once daily, or less frequently such as 1-6 times per week. Treatments of inflammations may span between about 1 to 10 weeks (e.g., between 2 to 8 weeks, between 3 to 7 weeks, for about 1, 2, 3, 4, 5, 6, 7, 8, 9, or 10 weeks). Administering anatabine glutarate to prevent inflammations may be conducted for infinite time spans and the doses may be adjusted accordingly. Anatabine glutarate may be administered for infinite time spans to prevent and treat substance addiction as needed to satisfy cravings, or at intervals such as once daily, twice daily, or three or more times daily, depending on such factors as the amount of anatabine glutarate and the subject's physiological conditions. It will also be appreciated that a dose regimen used for treatment may increase or decrease over the course of a particular treatment.

Usually, the level of purity of the anatabine glutarate used in the present invention is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

The anatabine glutarate can be provided together with other ingredients, for example, in the form of an elixir, a solvate, a beverage, a chew, a tablet, a lozenge, a gum, and the like. In one embodiment, for example, a beverage may be in the form of a bottled water product containing about 100 ml to about 2,000 ml purified water and from about 0.00001 to about 0.0001 wt % of a water-soluble salt of anatabine glutarate. Additional inactive ingredients may be added to improve product characteristics, such as taste, color/clarity, and/or stability. The bottled water product may also contain other beneficial components, such as vitamins, proteinaceous ingredients, or the like. A composition alternatively may be provided in a solid (e.g., powder) form, such as in a packet, which can be combined with water or other liquid (e.g., by an end user) to prepare a beverage.

Pharmaceutical compositions comprising the compounds, crystals or polymorphic forms of the present invention may be formulated together with one or more pharmaceutically acceptable excipients. As used herein, the term "pharmaceutically acceptable excipient" means a nontoxic, inert solid, semisolid or liquid filler, diluent, encapsulating material or formulation auxiliary of any type. For example, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar, buffering agents such as magnesium hydroxide and aluminum hydroxide; alginic acid; pyrogen-free water; isotonic saline; Ringer's solution; ethyl alcohol, and phosphate buffer solutions, as well as compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Liquid pharmaceutical compositions for use in thermal vaporization aerosol devices typically contains other components such as water, organic solvents, sweetening and/or flavoring agents, and the like. Examples of solvents that are commonly used in liquid compositions for thermal vaporization aerosol devices include polyhydric alcohols such as 1,2-propylene glycol (PG or MPG); monohydric alcohols such as ethanol; ethyl acetate; and the like. The amount of water present typically ranges from about 0.1 to about 10 wt. %, usually from about 0.5 to about 5 wt. %. The amount of organic solvent present typically ranges from about 50 to about 99 wt. %, often from about 75 to about 95 wt. %. If desired, one or more flavorants may be added to the composition, non-limiting examples of which include peppermint, menthol, wintergreen, spearmint, propolis, *eucalyptus*, cinnamon, or the like. The total amount of flavorants typically ranges from about 0.5 to about 15 wt. %, often from about 1 to about 10 wt. %, based on the total weight of the composition. By way of example, the amount of anatabine glutarate may range from about 0.1 to about 25 mg, from about 0.5 to about 20 mg, or from about 1 to about 10 mg, per total gram of composition.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents. Solid dosis forms of the invention may be formulated for slow release.

In order to prolong the effect of the compound, the crystal, the polymorph and/or the pharmaceutical composition of the invention, it is often desirable to slow the absorption of the substance from subcutaneous or intramuscular injection. This may be accomplished by the use of a liquid suspension of crystalline or amorphous material with poor water solubility. The rate of absorption of the substance then depends upon its rate of dissolution, which, in turn, may depend upon crystal size and crystalline form. Alternatively, delayed absorption of a parenterally administered substance form is accomplished by dissolving or suspending the substance in an oil vehicle. Injectable depot forms are made by forming microencapsule matrices of the substance in biodegradable polymers such as polylactide-polyglycolide. Depending upon the ratio of substance to polymer and the nature of the particular polymer employed, the rate of substance release can be controlled. Examples of other biodegradable polymers include poly(orthoesters) and poly(anhydrides). Extended release formulations are known in the art. For example, swellable particles are taught in U.S. Pat. Nos. 5,582,837, 5,972,389, and 6,723,340. Polymer matrices are taught in U.S. Pat. Nos. 6,210,710, 6,217,903, and 6,090,411. Typical materials used for extended release formulations are the polymers poly(ethylene oxide) and hydroxypropyl methylcellulose. Depot injectable formulations are also prepared by entrapping the substance in liposomes or microemulsions that are compatible with body tissues.

The pharmaceutical compositions may be prepared by any suitable technique and are not limited by any particular method for their production. For example, anatabine glutarate can be combined with excipients and a binder, and then granulated. The granulation can be dry-blended with any remaining ingredients, and compressed into a solid form such as a tablet.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

The pharmaceutical compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

The compounds, crystals, polymorphic forms and pharmaceutical compositions of the present invention may be administered by any suitable route. For example, the compositions may be administered orally, parenterally, by inhalationtopically, rectally, nasally, buccally, vaginally, via an implanted reservoir, or ingested as a dietary supplement or food. The term parenteral as used herein includes subcutaneous, intracutaneous, intravenous, intramuscular, and intracranial injection or infusion techniques. Preferred routes of administration include inhalation via a dry powder inhaler or vaporization aerosol devices such as a thermal vaporization aerosol device. Thermal vaporization aerosol devices are described, for example, in WO 02/098496, WO 02/098389 and WO 03/095012.

One aspect of the invention relates to the compound, the crystal or the polymorphic form of the present invention, or the pharmaceutical composition for use according to the invention in a thermal vaporization aerosol device. Ie amount of anatabine glutarate may vary depending on factors such as the type of the thermal vaporization aerosol device and whether other active components are present.

The thermal vaporization aerosol device may be of various types of configurations, the details of which form no part of the present invention. In general, thermal vaporization aerosol devices may be of a single-use or disposable type, or may be refillable with liquid alkaloid compositions and/or cartridges containing liquid compositions to facilitate reuse.

Another aspect of the invention relates to the compound, the crystal or the polymorphic form of the present invention, or the pharmaceutical composition for use according to the invention in a dry powder inhaler. Using the dry powder inhaler technology, the packets of dry powder anatabine glutarate formulation loaded into the device can contain different amounts, for example 0.01 to 10 mg of anatabine glutarate per dose, 0.05 to 5 mg anatabine glutarate per dose or 0.1 to 1 mg of anatabine glutarate per dose, or different concentrations of anatabine glutarate can be made in different particle sizes and may contain formulations that modulate the rate of release and absorption of anatabine glutarate into the body following inhalation.

They may also have pH-modulators and additives affecting taste, smell and color. The aerosolization of the anatabine glutarate powder formulation can be accomplished using the user's breathing as the energy source, or compressed gas, or a battery that drives an electric motor with a propeller or a source of vibrations that disperse the powder.

By providing the compound, the crystal or the polymorphic form of the present invention, or the pharmaceutical composition for use according to the invention in a dry powder inhaler or a thermal vaporization aerosol device the cravings for traditional tobacco smoking may be reduced, while minimizing toxicity and other undesirable side effects associated with nicotine and other tobacco components. The dry powder inhaler or thermal vaporization aerosol device may be used as needed to satisfy cravings, or at intervals such as once daily, twice daily, or three or more times daily, depending on such factors as the concentration of active components and the subject's physiological conditions.

The invention thus also relates to a smokeless tobacco product comprising the compound, the crystal, the polymorph and/or the pharmaceutical composition of the invention.

The smokeless tobacco product contains a powdered form of the compound, the crystal, the polymorph and/or the pharmaceutical composition of the invention. In one embodiment, the smokeless tobacco product thus contains tobacco together with the compound, the crystal, the polymorph and/or the pharmaceutical composition of the invention In one preferred embodiment of the present invention, the smokeless tobacco product is a solid bit comprising powdered tobacco and the compound, the crystal, the polymorph and/or the pharmaceutical composition of the invention. The powdered tobacco may be produced from cured tobacco stems, lamina, or both (hereinafter collectively referred to as "tobacco material"). The relative proportion of tobacco material in the smokeless tobacco product depends on such factors as the particular composition of the tobacco leaf. The solid bit most often has from about 10% to about 80% of powdered tobacco by weight, more usually from about 25% to about 55% by weight.

Preferably, the cured tobacco material is pulverized, e.g. milled, to form a powdered tobacco. In this manner, the tobacco material is milled fine enough to produce an easily swallowed product. Alternatively, an extract of the tobacco material is dried to form a powder. In the extraction process, cured tobacco material is extracted with a solvent, typically water or steam. The resulting solution contains the water-soluble components of the tobacco, including nicotine. The solution is then dried and ground, as needed, to form a powdered tobacco.

The powdered tobacco may then be used to form a bit. Prior to forming the bit, however, the powdered tobacco may need to be processed to form larger particles such as by granulation or by rolling and grinding. Such processes provide particles, which are more readily formed into bits, and form bits, which do not disintegrate during handling and in the package. Moreover, the larger particles are easier to handle than the smaller particles and do not form the "dust" associated with small powder particles. Furthermore, the larger particles compress into bits more readily than powder particles. This allows for higher speed bit formulation and easier machining of the bits. In addition, using either granulation or rolling and pressing provides an even distribution of flavorants, coloring agents, and the like, throughout the final bit.

Other aspects of the present invention are directed to the compound, the crystal, the polymorph and/or the pharmaceutical composition of the invention for e-cigarettes which are designed to provide different ranges of an alkaloid composition comprising the compound, the crystal, the polymorph and/or the pharmaceutical composition of the invention to more effectively achieve the pleasure-enhancing effects that smokers obtain through smoking traditional cigarettes, while avoiding or reducing exposure to nicotine. In one embodiment, the alkaloid composition comprises at least about 25 wt. % of the compound, the crystal, the polymorph and/or the pharmaceutical composition of the invention based on the total alkaloid weight. In some examples, the compound, the crystal, the polymorph and/or the pharmaceutical composition of the invention is the sole alkaloid present in the composition, e.g., the compound, the crystal, the polymorph and/or the pharmaceutical composition of the invention comprises 100 wt. % of the total alkaloid weight. In other examples, up to about 75 wt. % of one or more other alkaloids, such as nicotine, nornicotine, and/or anabasine, may be present in addition to the compound, the crystal, the polymorph and/or the pharmaceutical composition of the invention. For example, the compound, the crystal, the polymorph and/or the pharmaceutical composition of the invention and nicotine may be combined in a weight ratio (anatabine-to-nicotine) of about 50:1 to about 1:3, or from about 25:1 to about 1:2, from about 10:1 to about 3:2, or from about 5:1 to about 1:1.

The amount of the compound, the crystal, the polymorph and/or the pharmaceutical composition of the invention present in the composition may vary depending on factors such as the type of e-cigarette and whether other active components, such as nicotine and/or other alkaloids, are present. By way of example, the amount of the compound, the crystal, the polymorph and/or the pharmaceutical composition of the invention may range from about 0.1 to about 25 mg, from about 0.5 to about 20 mg, or from about 1 to about 10 mg, per total gram of composition.

In addition to the compound, the crystal, the polymorph and/or the pharmaceutical composition of the invention, the composition may contain up to about 75 wt. % of one or more other alkaloids, such as nicotine, nornicotine, and/or anabasine, based on the total alkaloid weight. Such alkaloids may be extracted from tobacco or other plant materials and purified using known techniques, and/or prepared synthetically using known synthesis methods. The compound, the crystal, the polymorph and/or the pharmaceutical composition of the invention and additional alkaloid(s), such as nicotine, may be combined in a weight ratio (anatabine-to-total other alkaloids) of about 50:1 to about 1:3, or from about 25:1 to about 1:2, from about 10:1 to about 3:2, or from about 5:1 to about 1:1.

The composition typically contains other components such as water, organic solvents, sweetening and/or flavoring agents, and the like. Examples of solvents that are commonly used in liquid compositions for e-cigarettes include polyhydric alcohols such as 1,2-propylene glycol (PG or MPG); monohydric alcohols such as ethanol; ethyl acetate; and the like. The amount of water present typically ranges from about 0.1 to about 10 wt. %, usually from about 0.5 to about 5 wt. %. The amount of organic solvent present typically ranges from about 50 to about 99 wt. %, often from about 75 to about 95 wt. %.

If desired, one or more flavorants may be added to the composition, non-limiting examples of which include peppermint, menthol, wintergreen, spearmint, propolis, *eucalyptus*, cinnamon, or the like. The total amount of flavorants typically ranges from about 0.5 to about 15 wt. %, often from about 1 to about 10 wt. %, based on the total weight of the composition.

The e-cigarette may be of various types of configurations. In general, e-cigarettes may be of a single-use or disposable type, or may be refillable with liquid alkaloid compositions and/or cartridges containing liquid compositions to facilitate reuse. One example of an e-cigarette is shown in FIG. 1 of U.S. Ser. No. 15/679,731. An air inlet is provided on the external wall of a shell which houses LED, cell, electronic circuit board, normal pressure cavity, sensor, vapor-liquid separator, atomizer, liquid-supplying bottle, mouthpiece, microswitch, gas vent, and air passage. The electronic circuit board has an electronic switching circuit and a high frequency generator. A negative pressure cavity is provided in the sensor and is separated from the sensor by a ripple film. An atomization cavity is provided in the atomizer. A retaining ring is provided for locking the liquid-supplying bottle between one side of the liquid-supplying bottle and the shell; and an aerosol passage is provided on the other side of the liquid-supplying bottle. Other details are described in U.S. Pat. No. 7,832,410 B2 to Hon, the disclosure of which is hereby incorporated by reference in its entirety.

By providing a balanced alkaloid composition containing the compound, the crystal, the polymorph and/or the pharmaceutical composition of the invention as a significant alkaloid component, it is possible to prepare e-cigarettes that reduce cravings for traditional tobacco smoking, while minimizing toxicity and other undesirable side effects associated with nicotine and other tobacco components. The e-cigarette may be used as needed to satisfy cravings, or at intervals such as once daily, twice daily, or three or more times daily, depending on such factors as the concentration of active components and the subject's physiological conditions.

In an alternative embodiment, a non-tobacco formulation contains an alkaloid composition comprising about 25 wt. % to about 95 wt. % anatabine, and about 5 wt. % to about 75 wt. % of a second alkaloid, based on the total alkaloid weight of the composition. The second alkaloid may be nicotine, nornicotine, anabasine, or a combination of two or more of them. The non-tobacco product may be in the form of a solid bit of compressed powder, chewing gum, capsule, pill, lozenge, or the like. The term "non-tobacco" means that the product is essentially free of tobacco leaf or tobacco extract, except however that some or all of the alkaloids present in the non-tobacco product may be extracted from tobacco and purified using conventional techniques such as liquid chromatography.

Additional components ingredients may be added to the non-tobacco products to improve taste or stability. Such additional components include, but are not limited to, sweeteners, natural flavorants, artificial flavorants, colorants, antioxidants, preservatives, chelating agents, viscomodulators, tonicifiers, odorants, opacifiers, suspending agents, binders, thickeners, and mixtures thereof, including, but not limited to, xanthum gum, carboxymethylcellulose, carboxyethylcellulose, hydroxypropylcellulose, methylcellulose, microcrystalline cellulose, starches, dextrins, fermented whey, tofu, maltodextrins, polyols (including sugar alcohols, such as sorbitol or mannitol), carbohydrates (e.g., lactose), propylene hlycol alginate, gellan gum, guar, pectin, tragacanth gum, gum acacia, locust bean gum, gum arabic, gelatin, mannitol, natural and/or artificial mint flavors, sucralose, silicon dioxide, stearic acid, hydroxypropyl methylcellulose, magnesium stearate, titanium dioxide, natural glaze, methylparaben, propylparabens, triethyl citrate, citric acid, butylated hydroxytoluene (BHT), mono and diglycerides, polysorbate 80, and the like.

The non-tobacco products may be in a variety of forms, e.g., to be taken orally, such as pills, tablets, capsules, soft gels, gelcaps, liquids, syrups, suspensions, powders, chews, lozenges, gum, bars, etc., or to be administered by other routes, such as parenterally, by inhalation spray, topically, via an implanted reservoir, etc. The alkaloid compositions also can be prepared to be administered in foods or beverages. For example, they can be supplied as a dried or powdered product for reconstitution with water or other suitable vehicle before use (e.g., milk, fruit juice, and the like).

The compound, crystal, polymorph and/or the pharmaceutical composition or any other composition provided herein, may further comprise one or more vitamins, such as Vitamin A (retinol), Vitamin B1 (thiamine), Vitamin C (ascorbic acid), Vitamin D (calciferol), Vitamin D2 (ergocalciferol), Vitamin D3 (cholecalciferol), Vitamin B2 (riboflavin), Vitamin E (tocopherol), Vitamin B12 (cobalamins), Vitamin K1 (phylloquinone), Vitamin B5 (pantothenic acid), Vitamin B7 (biotin), Vitamin B6 (pyridoxine), Vitamin B3 (niacin), Vitamin B9 (folic acid). Methods of synthesizing vitamins are well known, and vitamins can be obtained from any reputable commercial source. In some embodiments, the compound, crystal, polymorph and/or pharmaceutical composition of the invention further comprises Vitamin A. In some embodiments, the compound, crystal, polymorph and/or pharmaceutical composition of the invention further comprises Vitamin D3. In some embodiments, the compound, crystal, polymorph and/or pharmaceutical composition of the invention further comprises Vitamin A and Vitamin D3.

The amount of anatabine and vitamins in compositions of the present invention may vary. In some embodiments, the amount of the compound, crystal, polymorph ranges from about 0.1 mg to about 10 mg (e.g. about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, or 10 mg).

In some embodiments, the amount of Vitamin A ranges from about 200 to about 500 IU (e.g., about 200, 250, 300, 350, 400, 401, 402, 403, 404, 405, 406, 407, 408, 409, 410, 411, 412, 413, 414, 415, 416, 417, 418, 419, 420, 450, 475, or 500 IU). Vitamin A can be provided, for example, as retinyl acetate.

In some embodiments, the amount of Vitamin D3 ranges from about 15 IU to about 50 IU (e.g., about 15, 20, 25, 26, 27, 28, 29, 30, 31, 32, 33, 34, 35, 40, 45, or 50 IU). Vitamin D3 can be provided as cholecalciferol.

In some embodiments the compound, crystal, and/or polymorph and Vitamin A are provided in equal proportions (e.g., 1 mg each). In some embodiments, one or two lozenges containing 1 mg of the compound, crystal, and/or polymorph can be taken once, twice, or three times daily. In some embodiments, daily doses do not exceed 1, 2, 3, 4, 5, or 6 lozenges. In some embodiments, daily doses can exceed 1, 2, 3, 4, 5, or 6 lozenges. In some embodiments a product is in the form of a lozenge that contains 1 mg of the compound, crystal, polymorph and/or composition of the invention, 417 IU Vitamin A (as retinyl acetate), 33 IU Vitamin D3 (as cholecalciferol), and mannitol, natural and artificial mint flavors, sucralose, silicon dioxide, stearic acid, hydroxypropyl methylcellulose, magnesium stearate, titanium dioxide, natural glaze, methyl parabens, propylparabens, triethyl citrate, citric acid, BHT, mono and diglycerides, and polysorbate 80.

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

Example 1

Preparation of Anatabine Glutarate

Anatabine free base was converted to 1:1 anatabine glutarate by the following methods:

a) To a solution of glutaric acid (16.5 g, 125 mmol, 1.00 eq) in acetonitrile (500 mL) was added anatabine (20.0 g, 125 mmol, 1.00 eq) drop-wise at 25° C., and the mixture was stirred at 25° C. for 1 hour. TLC (Dichloromethane: Methanol=20:1) showed anatabine (Rf=0.5) was consumed. The mixture was filtered. The filter cake was collected and concentrated to dryness to give anatabine glutarate (30.0 g, 103 mmol, 82.2% yield, 100% purity) as an off-white solid.

b) To a solution of anatabine (11.6 g, 72 mmol) in acetonitrile (700 ml) was added glutaric acid (9.6 g, 72 mmol). The reaction mixture became cloudy. The reaction mixture was then heated until a clear yellow solution was obtained. The mixture was allowed to cool to room temperature (20° C.) and was stirred for 2 hours. A gummy solid appeared which was scratched with a spatula. The mixture was stirred for a further 30 minutes, and the resulting pale-yellow solid was filtered under an atmosphere of argon, washed with acetonitrile (500 ml) and dried under reduced pressure at 45° C. for 45 minutes to give anatabine glutarate (18.3 g, 87%) as a pale yellow solid.

$^1$HNMR (D$_2$O), δ: 8.84-8.45 (m, 2H), 7.99 (d, J=7.8 Hz, 1H), 7.59-7.55 (m, 1H), 6.08 (d, J=8.4 Hz, 1H), 5.85 (d, J=10.4 Hz, H), 4.63-4.59 (m, 1H), 3.97-3.87 (m, 1H), 3.81-3.70 (m, 1H), 2.80-2.53 (m, 2H), 2.25 (t, J=7.6 Hz, 4H), 1.82-1.74 (m, 2H). The chemical purity of anatabine glutarate was assessed using Waters Acquity UPLC H-class with PDA detector and SQD mass spectrometer, column BEH C18, 2.1×50 mm, 1.7 μM running a gradient with detection at 261 nM. The retention time of anatabine glutarate was 1.125 min and purity 99.41%, [M+H]$^+$ 161.0 (FIG.

Figure 5:
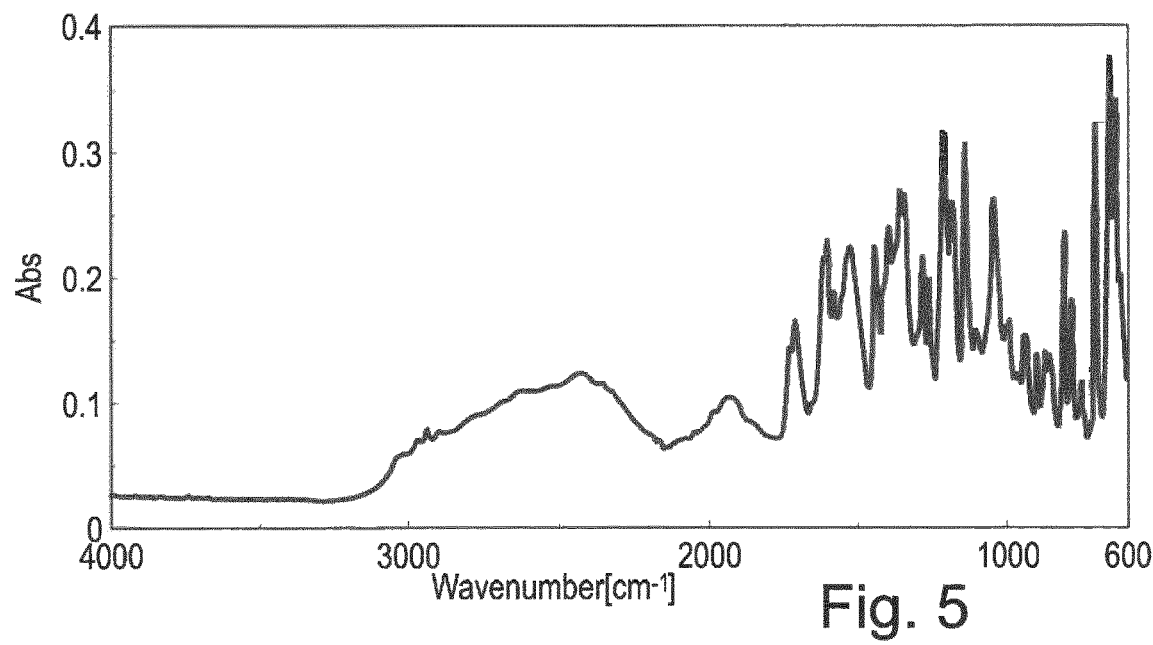
FIG. 5: FTIR spectrum of anatabine glutarate
Figure 6:
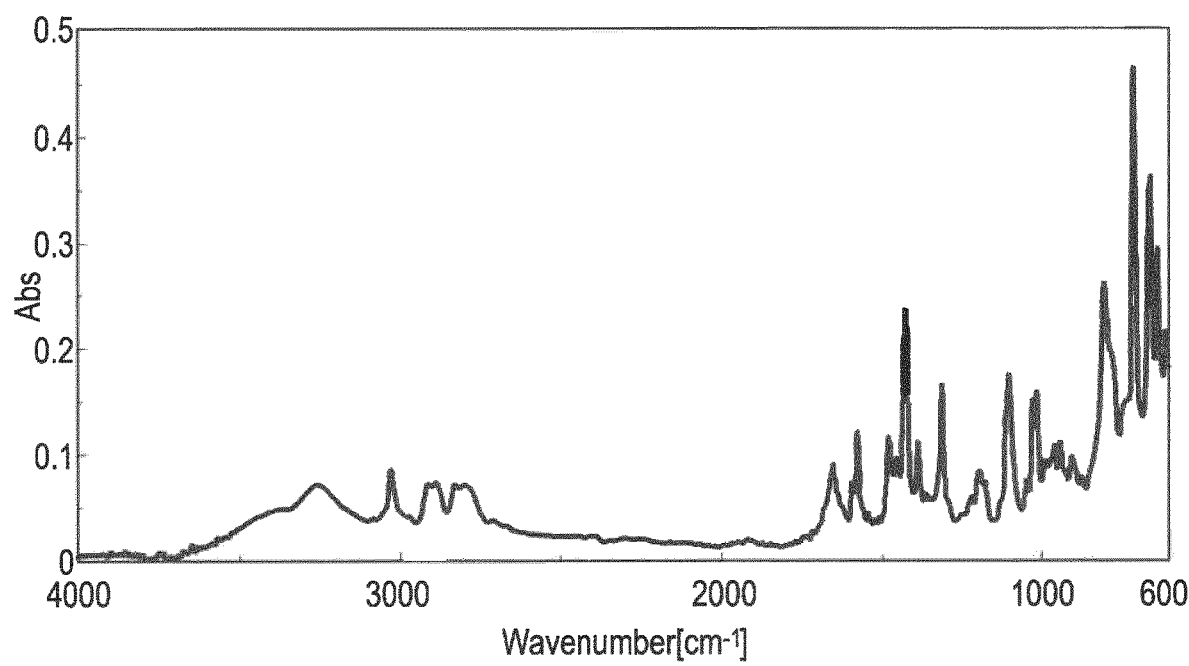
FIG. 6: FTIR spectrum of anatabine free base
Figure 7:
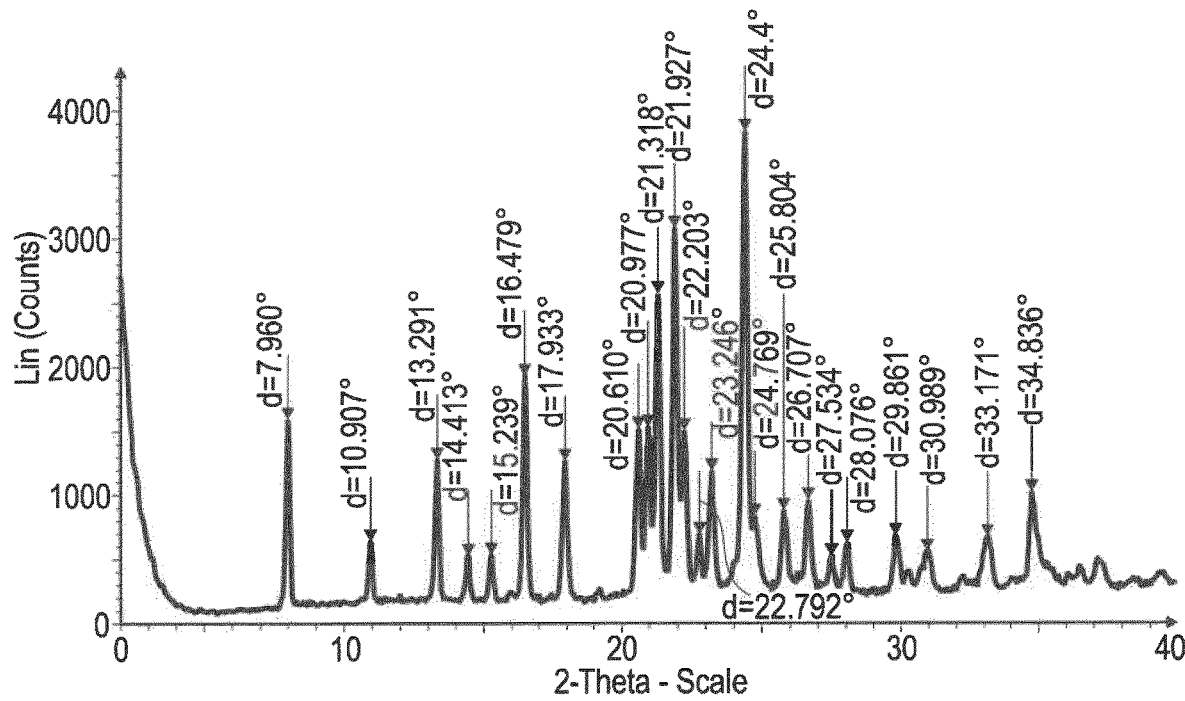
FIG. 7: X-ray diffractogram of anatabine glutarate with peak positions
Figure 8:
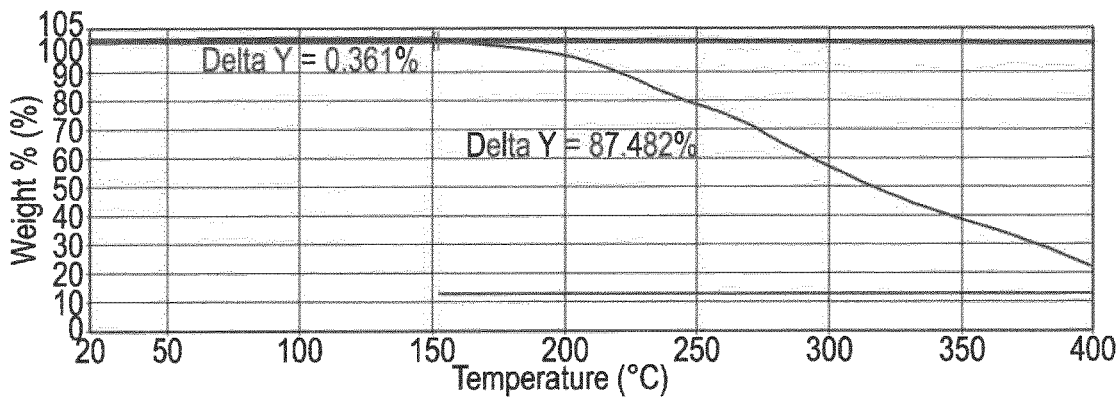
FIG. 8: TGA thermogram of anatabine glutarate
Figure 9:
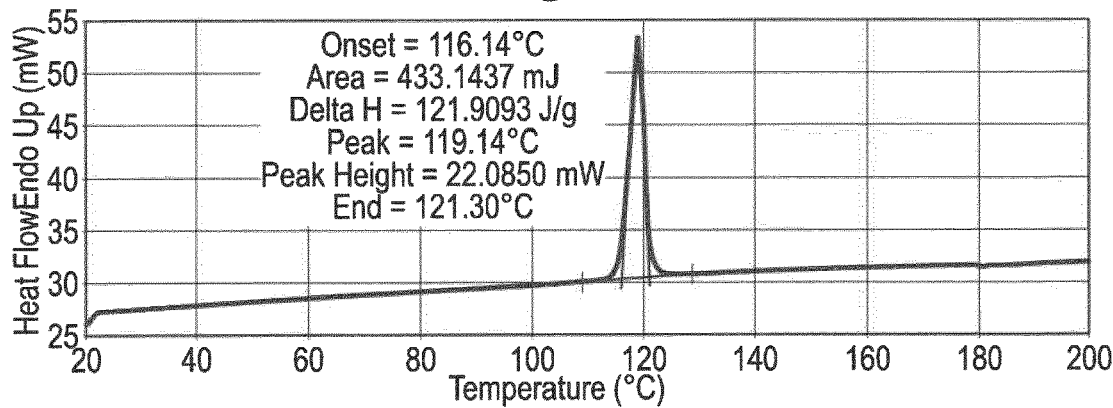
FIG. 9: DSC thermogram of anatabine glutarate

3, 4). Comparison of FTIR spectra of anatabine glutarate (FIG. 5) and anatabine free base (FIG. 6) indicates change of N—H band suggesting confirmation of salt formation.

The anatabine glutarate obtained in this manner was recrystallized from 2.5 mL actonitrile while cooling down after having been heated to reflux. The solid phase was recovered and dried.

The anatabine glutarate salt was analyzed by X-ray powder diffraction (XRPD) between 2-40 °2Θ using zero background silicone wafers (with 9 mm cavities). It was found to have a purity higher than 99% by uHPLC.

Example 2

Ion Chromatography of Anatabine Glutarate

Figure 11:
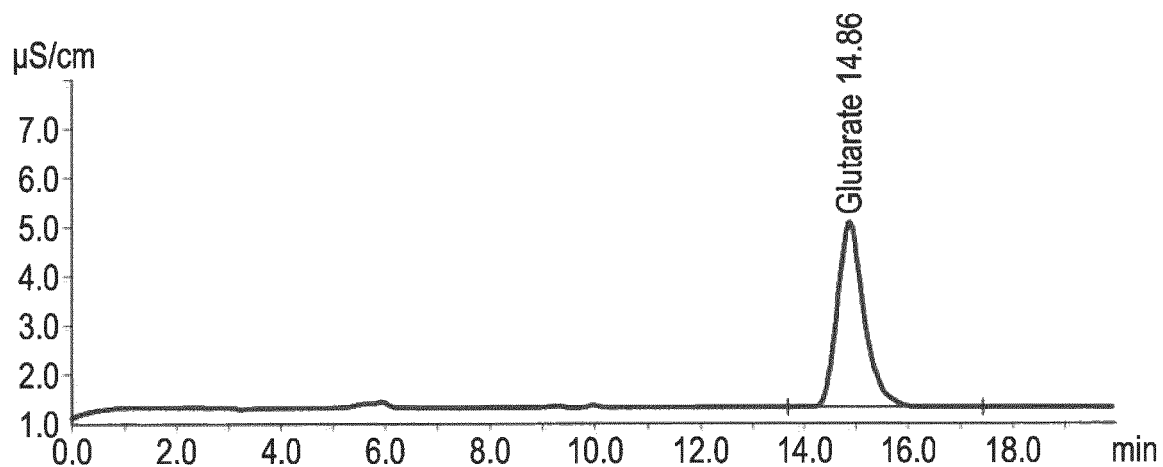
FIG. 11: Ion chromatogram of anatabine glutarate

Ion chromatography analysis was conducted to analyze the stoichiometry of anatabine glutarate (FIG. 11). Anatabine glutarate was dissolved in IC grade water (90 µg/ml), the solution was analyzed on Metrohm 940 high pressure gradient ion chromatograph with Metrohm 889 cooled autosampler, eluent solution 3.2 mM sodium carbonate and 1 mM sodium bicarbonate, regeneration solution 150 mM sulfuric acid/100 mM oxalic acid using column A Supp 5 (IC004 or equivalent). Anatabine glutarate was analyzed twice, the results are summarized in the following table:

| Sample | Peak Area | Conc. found (% w/w) | Av. Conc. found (% w/w) | Av. Theoretical Recovery (w-%) |
| --- | --- | --- | --- | --- |
| 1 | 2.3128 | 43.82 | 43.90 | 98.0 |
| 2 | 2.3194 | 43.98 | | |

Figure 2:
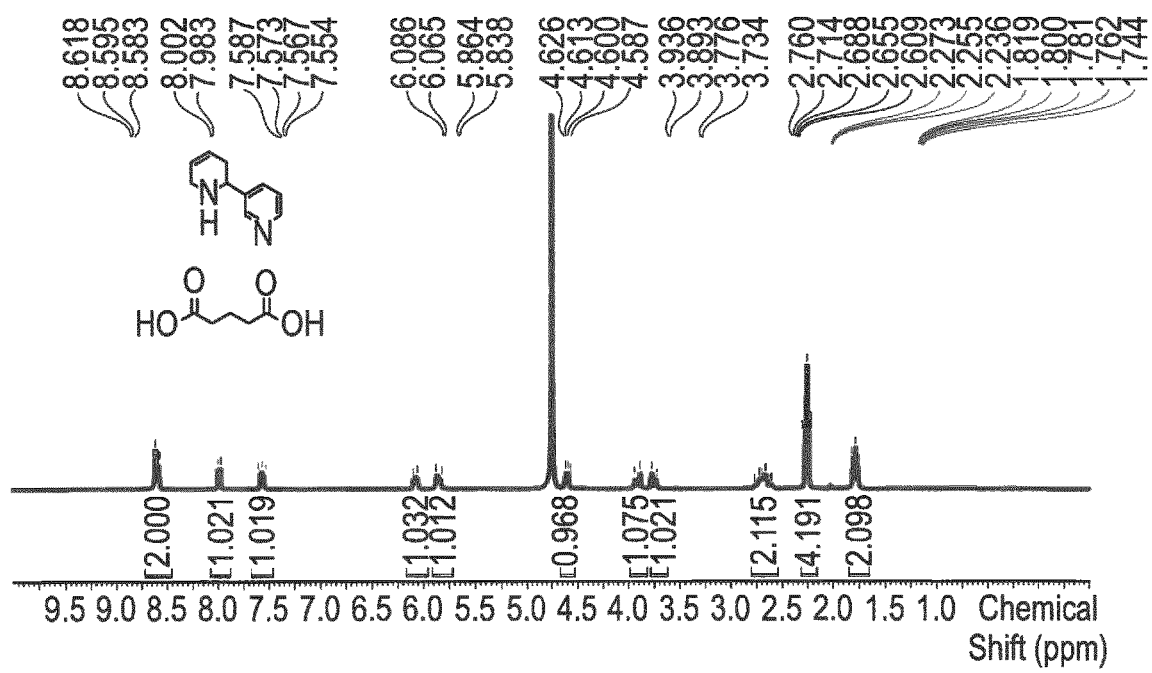
FIG. 2: $^1$H NMR spectrum of anatabine glutarate obtained in Example 1
Figure 3:
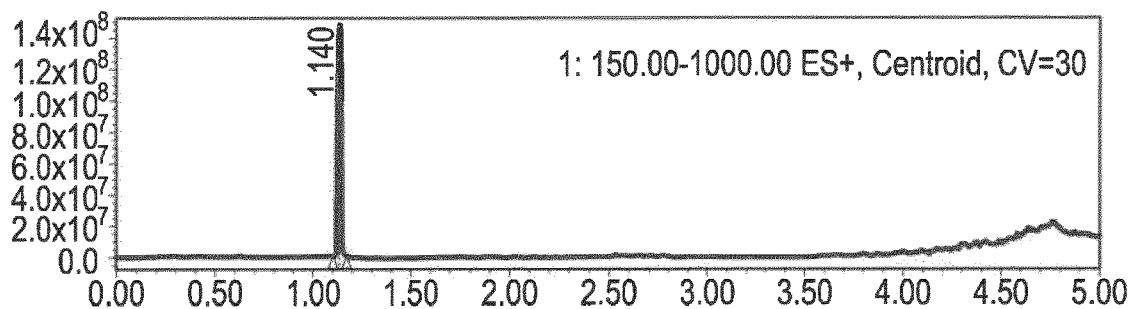
FIG. 3: Total ion current chromatogram of anatabine glutarate in positive ionization mode
Figure 4:
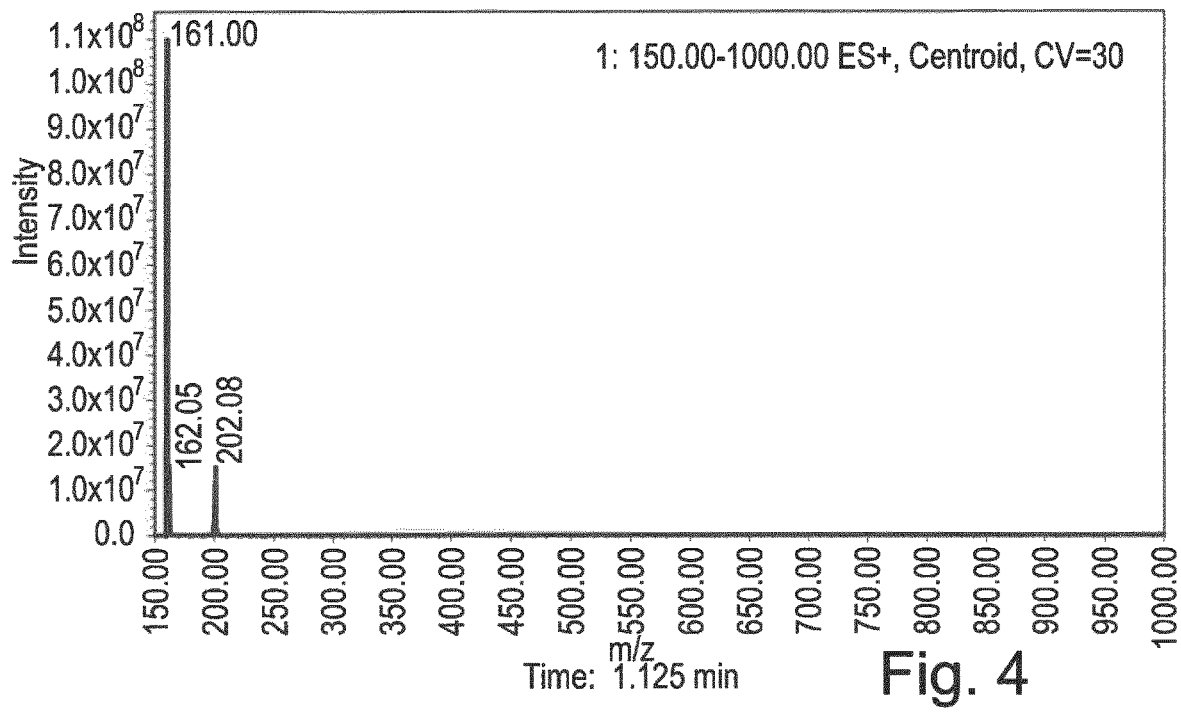
FIG. 4: Mass spectrum of anatabine glutarate in positive ionization mode

The theoretical recovery of 98.0% confirms the presence of glutarate in a ratio of 1:1 anatabine:glutarate. The results of ion chromatography are consistent with the proton NMR spectrum (FIG. 2).

Example 3

Dynamic Vapor Sorption Testing of Anatabine Glutarate

Figure 10:
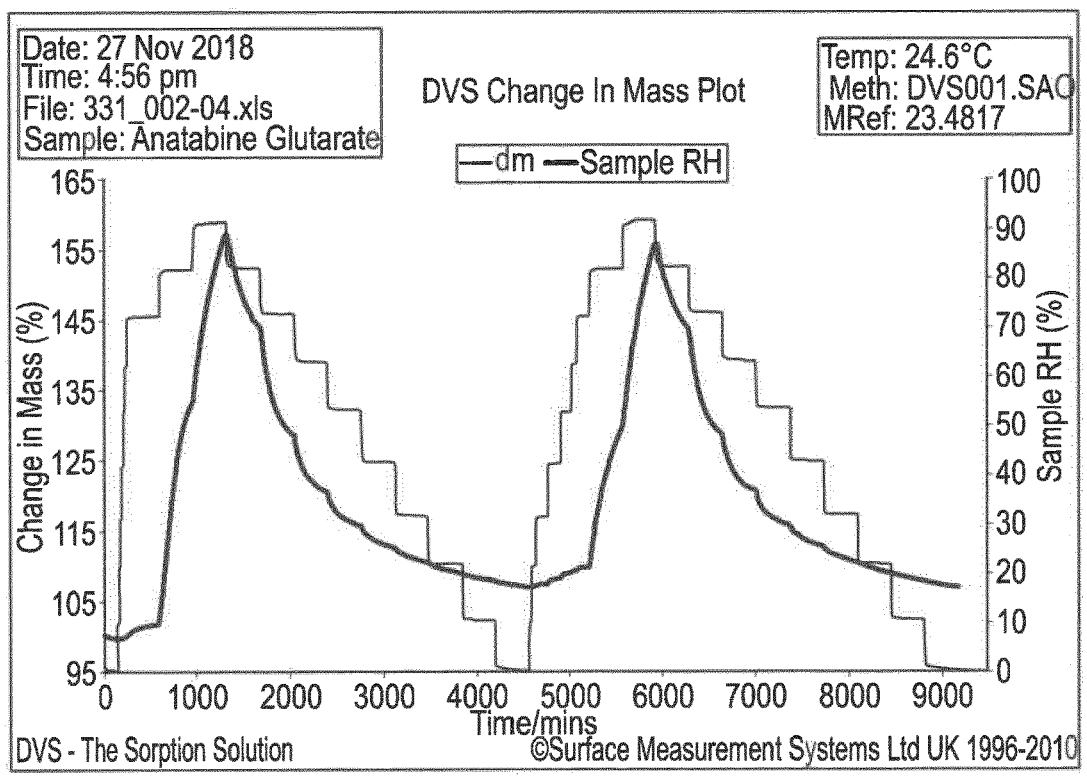
FIG. 10: DVS plot of anatabine glutarate

Anatabine glutarate (20 mg) was dispensed directly into a pre-weighed sample pan and transferred to the instrument (DVS1 Advantage). Double cycle 0-90-0-90-0% RH method with 10% RH steps was applied. The sample showed 55% mass gain on first sorption cycle, whereas the majority of the mass gain occurs above 70% RH. The first desorption cycle shows about 50% mass loss, which is repeated in the second cycle with only about 50% mass gain in the second sorption cycle. This mass gain is confirmed in isotherm which shows about 5% mass gain between the starting weight and the end weight (FIG. 10).

Example 4

Karl Fischer Titration of Anatabine Glutarate

The amount of water in obtained anatabine glutarate was determined on Metrohm 852 Combined Volumetric/Coulometric Karl Fischer Titrando with 860 Oven using 100 mg of the sample. The anatabine glutarate was found to contain 0.21% w/w water.

Example 5

Stability Assessment of Anatabine Glutarate

Anatabine glutarate was analyzed at T=0, and an aliquot subsequently stored in a glass vial with a screw cap lid at accelerated conditions (40° C./75% RH) in an incubator for 7 days prior to further analysis. The stored sample was visually assessed for stability at T=0, 3 and 7 days with no change observed in the color or any evidence of deliquescence. The stored sample was also assessed at T=0 and again post T=7 days using TGA, XRPD and HPLC-UV.

The TGA thermogram of the T=7 days sample showed a slight mass loss between 20-130° C. of 0.5%, whereafter degradation occurred and 80% mass loss occurred between 150° C. and 400° C. The superposition of the thermograms at days T=0 and T=7 showed little difference, with only a 2% difference in mass loss. It can thus be seen that there was no change in thermal stability when anatabine glutarate was stored at 40° C./75% RH for 7 days.

The XRPD pattern of the T=7 days sample shows no difference from the T=0 pattern and the material remained in the same, therefore indicating that there was no change to the crystalline form of anatabine glutarate when stored at 40° C./75% RH for 7 days.

For evaluation of stability by HPLC-UV, 200 µg/ml sample solution of anatabine and anatabine glutarate were prepared in duplicate by weighing approximately 10 mg and dissolving in 50 ml volumetric flask and bringing to the volume with deionized water. During the HPLC method optimization the run time and gradient have been adjusted for stability analysis. After the method optimization, a forced degradation trial was run to aid the planned stability assessment analysis by identifying any degradants or impurities present in the anatabine glutarate sample. The forced degradation trial analyzed samples under five conditions—acid, base, control, heat and oxidation—and were tested at T=0, 4 and 18 hours. The only sample, which demonstrated any degradation (>1% by peak area) was the oxidized sample, in which 3% hydrogen peroxide ($H_2O_2$) had been added.

Figure 12:
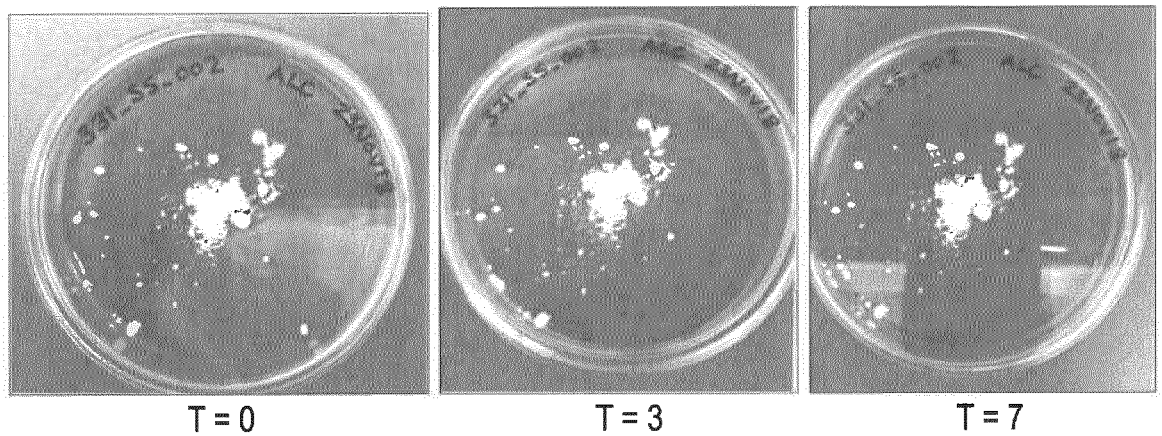
FIG. 12: Ambient stability sample of anatabine glutarate at T=0, 3 and 7 days.

For ambient stability assessment, anatabine glutarate (100 mg) was weighed into a clear glass Petri dish and retained at ambient conditions, open in a fume hood for 7 days. The stored sample was visually assessed at T=0, 3 and 7 days. No change in the color or any evidence of deliquescence were observed (FIG. 12).

Comparative Example 1

Preparation of Anatabine Citrate

Anatabine free base (160 mg, 1 mmol) was dissolved in anhydrous acetone (2.5 ml). To the formed solution was added a solution of anhydrous citric acid (192 mg, 1 mmol) in anhydrous acetone (3 ml, required sonication) with stirring under nitrogen. The mixture was stirred for 2 hours and then filtered under a blanket of nitrogen. The solid was washed with a small quantity of anhydrous acetone and dried in vacuo. A yield of 340 mg (96.6%) of anatabine citrate was achieved. As this salt has been demonstrated to be extremely hygroscopic, it was stored under nitrogen. Chemical structure and stoichiometry was confirmed by proton NMR. The solid form of the citrate contains captured acetone.

The tartrate form was prepared analogously and both the tartrate (FIG. 13) and the citrate (FIG. 14) (disclosed in U.S. Pat. Nos. 8,207,346 and 8,557,999) were found to exist in an amorphous form.

General Procedures

Modulated differential scanning calorimetry (mDSC) was performed on Perkin Elmer DSC 8000 using 40 µL aluminum pans. About 6 mg of each sample was placed onto a pre-weighed aluminum DSC pan using an analytical balance. The sample was heated from −70 to 175° C. at 5° C.

using a temperature modulation program under a nitrogen atmosphere. The data was examined for any thermal events.

Fourier transform infrared spectroscopy (FT-IR) was performed on Jasco 420 FT-IR using attenuated total reflectance (ATR) module. 1-2 mg of sample was placed onto the crystal of the ATR module and secured into position. Analysis was performed using the Jasco Spectra Manager software v1.51.00.

Powder X-ray diffraction (XRPD) was performed on Bruker D8 Advance XRPD using 9 mm cavity and flat plate sample holders. Samples were prepared by coating them onto sample holders fitted with a zero background silicon wafer (5 1 0). Analysis was performed using a Cu Kα X-Ray source which operated at 40 kV at 40 mA and a Lynx Eye TM detector, all samples were analyzed over the range 2-40° 2θ.

Thermogravimetric Analysis (TGA) was performed on Perkin Elmer PYRIS 1 TGA using 40 μL aluminum pans (vented) in ceramic crucibles. The samples were heated from room temperature to 400° C. at 10° C./min (unless otherwise stated) under a stream of nitrogen gas.

$^1$H Nuclear magnetic resonance spectroscopy (NMR) was performed on Bruker 400 Avance spectrometer equipped with a 5 mm QNP probe. 5-7 mg of a sample was dissolved in deuterated methanol or dimethyl sulfoxide. Solution was transferred into field matched 5 mm NMR tubes for analysis.

Dynamic vapor sorption (DVS) was performed on SMS DVS dynamic vapor sorption instrument using DVS control software v1.0.6.0. 30 mg of sample was weighed in stainless steel DVS basket before submitting for analysis. The samples were analyzed over the range of 0-90/RH with a maximum time of 6 hours per humidity stage. Each sample was exposed to a double cycle. Analysis was performed as a weight percent change from 0-90% RH with isothermal plots also being examined. XRPD analysis of all samples was performed post-DVS.

Chemical integrity and stoichiometry of anatabine glutarate was confirmed by $^1$H-NMR spectroscopy.

Ion chromatography was performed on Metrohm 940 high pressure gradient ion chromatograph with Metrohm 889 cooled autosampler, eluent solution 3.2 mM sodium carbonate and 1 mM sodium bicarbonate, regeneration solution 150 mM sulfuric acid/100 mM oxalic acid.

DVS analysis of this sample showed a mass uptake of 55% between 0-90% RH on the first sorption cycle and then lost mass during desorption until it reached 5% above the starting mass. This indicates a gain of moisture. The second sorption cycle showed a mass uptake of 50% and after a second desorption, the final mass was 5% greater than of the starting mass.

This indicated that the water gained in the first sorption cycle has been retained. This was further confirmed by an isotherm plot of this sample.

After leaving the sample overnight, it was found to have recrystallized into a solid form. When comparing X-ray diffraction patterns of the sample before and after DVS a match was observed. This indicates that the crystal form before and after DVS was identical.

The anatabine glutarate has advantageous properties such as high crystallinity, morphology, thermal and mechanical stability to polymorphic conversion and/or to dehydration, storage stability, low content of residual solvent, a lower degree of hygroscopicity, flowability, and advantageous processing and handling characteristics.

The invention claimed is:

1. A polymorphic form of a crystal of a compound which is 3-(1,2,3,6-tetrahydropyridin-2-yl)pyridine glutarate or a pharmaceutically acceptable solvate thereof, wherein the polymorphic form has an X-ray powder diffraction pattern (CuKα) comprising one or more peaks selected from 8.0±0.2 °2θ, 11.0±0.2 °2θ, 13.3±0.2 °2θ, 16.5±0.2 °2θ, 18.0±0.2 °2θ, 20.7±0.2 °2θ, 21.0±0.2 °2θ, 21.4±0.2 °2θ, 22.0±0.2 °2θ, 22.3±0.2 °2θ, 23.3±0.2 °2θ and 24.5±0.2 °2θ.

2. The polymorphic form of a crystal of a compound according to claim 1, wherein the 3-(1,2,3,6-tetrahydropyridin-2-yl)pyridine glutarate has a 1:1 molar ratio of 3-(1,2,3,6-tetrahydropyridin-2-yl)pyridine to glutarate.

3. The polymorphic form of a crystal of a compound according to claim 1, wherein the 3-[1,2,3,6-tetrahydropyridin-2-yl]pyridine is 3-[(2S)-1,2,3,6-tetrahydropyridin-2-yl]pyridine.

4. The polymorphic form of a crystal of a compound according to claim 1, wherein the 3-[1,2,3,6-tetrahydropyridin-2-yl]pyridine glutarate has the following formula (I):

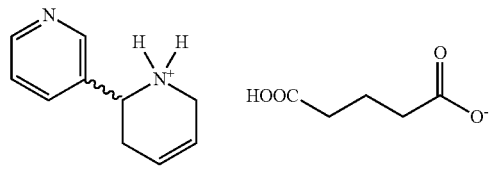 [SMILES: C1=CCC(c2cccnc2)[NH2+]C1 ; O=C([O-])CCCC(=O)O]

5. The polymorphic form of a crystal of a compound according to claim 1, wherein the 3-[1,2,3,6-tetrahydropyridin-2-yl]pyridine glutarate has the following formula (Ia):

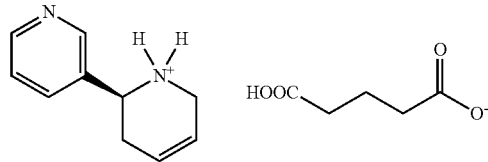 [SMILES: C1=CC[C@@H](c2cccnc2)[NH2+]C1 ; O=C([O-])CCCC(=O)O]

6. The polymorphic form according to claim 1, wherein the polymorphic form has an X-ray powder diffraction pattern (CuKα) substantially as shown in FIG. 1.

7. The compound according to claim 1 for use as a medicament.

8. The compound according to claim 1, for use in the treatment or prophylaxis of substance addiction or inflammation.

9. A pharmaceutical composition for use in the treatment or prophylaxis of substance addiction or inflammation, said composition comprising a pharmaceutically effective amount of the polymorphic form according to claim 1, optionally together with one or more pharmaceutically acceptable excipients.

10. A method for treating or preventing nicotine addiction or inflammation in a human or non-human animal patient in need thereof, wherein the method comprises administering to said patient a therapeutic effective amount of the polymorphic form according to claim 1.

11. A method for preparing the polymorphic form according to claim 1, comprising the steps of:
preparing a solution comprising 3-[1,2,3,6-tetrahydropyridin-2-yl]pyridine, glutaric acid and a solvent,
allowing the formation of a salt of 3-[1,2,3,6-tetrahydropyridin-2-yl]pyridine with the glutaric acid,
recovering the 3-[1,2,3,6-tetrahydropyridin-2-yl]pyridine glutaric acid salt, recrystallizing the 3-[1,2,3,6-tetrahydropyridin-2-yl]pyridine glutaric acid salt.

12. The method according to claim 11, wherein the solvent used in the preparation of the solution of 3-[1,2,3,6-tetrahydropyridin-2-yl]pyridine, glutaric acid and a solvent comprises 2-methyltetrahydrofuran, acetonitrile and/or ethyl acetate.

13. The polymorphic form according to claim 8, wherein the substance of the substance addiction is selected from the group consisting of nicotine, cocaine, heroine, marijuana, and alcohol.

14. The polymorphic form according to claim 8, wherein the inflammation is associated with one or more of Alzheimer's disease, thyroiditis, and multiple sclerosis.

15. A dry powder inhaler composition comprising the polymorphic form according to claim 8.

16. A thermal vaporization aerosol device composition comprising the polymorphic form according to claim 8.

* * * * *